US007679059B2

(12) United States Patent
Zhou

(10) Patent No.: US 7,679,059 B2
(45) Date of Patent: Mar. 16, 2010

(54) MEASURING WATER VAPOR IN HYDROCARBONS

(75) Inventor: Xin Zhou, Rancho Cucamonga, CA (US)

(73) Assignee: SpectraSensors, Inc., Rancho Cucamonga, CA (US)

( * ) Notice: Subject to any disclaimer, the term of this patent is extended or adjusted under 35 U.S.C. 154(b) by 0 days.

(21) Appl. No.: 11/715,599

(22) Filed: Mar. 7, 2007

(65) Prior Publication Data

US 2007/0246653 A1 Oct. 25, 2007

Related U.S. Application Data

(60) Provisional application No. 60/793,404, filed on Apr. 19, 2006.

(51) Int. Cl.
*G01J 3/42* (2006.01)
(52) U.S. Cl. .................. 250/343; 250/345; 250/339.13; 356/307
(58) Field of Classification Search .................. 250/343, 250/345, 339.13
See application file for complete search history.

(56) References Cited

U.S. PATENT DOCUMENTS

| | | | | |
|---|---|---|---|---|
| 4,829,183 | A | * | 5/1989 | McClatchie et al. .......... 250/346 |
| 4,953,390 | A | | 9/1990 | Krempl |
| 5,026,991 | A | | 6/1991 | Goldstein |
| 5,107,118 | A | * | 4/1992 | Murray et al. ............ 250/339.1 |
| 5,528,040 | A | | 6/1996 | Lehmann |
| 5,572,031 | A | | 11/1996 | Cooper et al. |
| 5,760,895 | A | | 6/1998 | Kebabian |
| 5,777,329 | A | | 7/1998 | Westphal et al. |
| 5,847,392 | A | * | 12/1998 | Van Den Berg et al. . 250/339.09 |
| 5,880,850 | A | | 3/1999 | McAndrew |
| 5,958,340 | A | | 9/1999 | Meyer et al. |
| 5,963,336 | A | | 10/1999 | McAndrew |
| 6,064,488 | A | | 5/2000 | Brand et al. |
| 6,188,475 | B1 | | 2/2001 | Inman et al. |
| 6,292,756 | B1 | | 9/2001 | Lievois et al. |

(Continued)

FOREIGN PATENT DOCUMENTS

| | | |
|---|---|---|
| DE | 3413914 A1 | 10/1985 |
| DE | 36 19 301 A1 | 12/1987 |
| EP | 0922908 | 6/1999 |
| GB | 2416205 | 1/2006 |
| WO | WO03/100393 | 12/2003 |
| WO | WO2005/047872 | 5/2005 |

OTHER PUBLICATIONS

"Olefin" Definition, Retrieved online [Dec. 7, 2008]; Retrieved from URL: <http:chemistry.about.com/library/glossary/bldef5880.htm.*

(Continued)

*Primary Examiner*—David P Porta
*Assistant Examiner*—Yara B Green
(74) *Attorney, Agent, or Firm*—Mintz, Levin, Cohn, Ferris, Glovsky & Popeo, P.C.

(57) ABSTRACT

Low concentrations of water vapor within a background of one or more olefin gases may be detected and quantified using a differential absorption spectrometer. A dehydrated sample of the gas is used as a background sample whose absorption spectrum allows elimination of absorption features not due to water vapor in the gas. Absorption spectra may recorded using tunable diode lasers as the light source. These lasers may have a wavelength bandwidth that is narrower than the water vapor absorption feature used for the differential absorption spectral analysis.

33 Claims, 11 Drawing Sheets

U.S. PATENT DOCUMENTS

| | | | | |
|---|---|---|---|---|
| 6,353,225 | B1* | 3/2002 | Strzoda et al. | 250/339.13 |
| 6,420,695 | B1 | 7/2002 | Grasdepot et al. | |
| 6,657,198 | B1* | 12/2003 | May | 250/339.13 |
| 6,762,836 | B2 | 7/2004 | Benicewicz et al. | |
| 6,841,781 | B2 | 1/2005 | Toomey | |
| 7,116,422 | B2 | 10/2006 | Larking et al. | |
| 7,132,661 | B2 | 11/2006 | May | |
| 7,176,464 | B2* | 2/2007 | Oka et al. | 250/343 |
| 7,193,718 | B2 | 3/2007 | Lundqvist et al. | |
| 7,228,017 | B2 | 6/2007 | Xia et al. | |
| 2002/0190840 | A1 | 12/2002 | Fujita et al. | |
| 2003/0213912 | A1 | 11/2003 | Tulip | |
| 2004/0034480 | A1 | 2/2004 | Binder | |
| 2004/0079887 | A1* | 4/2004 | May | 250/343 |
| 2004/0245471 | A1* | 12/2004 | May | 250/343 |
| 2006/0011844 | A1 | 1/2006 | Oka et al. | |
| 2006/0109470 | A1* | 5/2006 | May | 356/437 |
| 2006/0163483 | A1 | 7/2006 | Chabanis et al. | |
| 2006/0176486 | A1 | 8/2006 | Ho | |
| 2006/0192967 | A1* | 8/2006 | Kluczynski | 356/439 |
| 2008/0255769 | A1 | 10/2008 | Zhou et al. | |

OTHER PUBLICATIONS

Lancaster et al., Compact CH4 sensor based on difference frequency mixing of diode lasers in quasi-phasematched LiNbO3); Elsevier, Optics Communications (175) pp. 461-468; Published Mar. 1, 2000.*

Bomse, Davis S. et al., "Frequency modulation and wavelength modulation spectroscopes: comparison of experimental methods using a lead-salt diode laser", Applied Optics; 31(6): 718-731 (1992).

Brown, L.R. et al., "Experimental Line Parameters of the Oxygen A Band at 760 nm", Journal of Molecular Spectroscopy, 199: 166-179 (2000).

Cassidy, Daniel T. et al., "Atmospheric pressure monitoring of trace gases using tunable diode lasers", Applied Optics, 21(7): 1185-1190 (1982).

Cassidy, Daniel T. et al., "Trace gas detection with short-external-cavity InGaAsP diode laser transmitter modules operating at 1.58 μm", Applied Optics, 27(13): 2688-2693 (1988).

Herriott, Donald R. et al., "Folded Optical Delay Lines", Applied Optics, 4(8): 883-889 (1965).

Herriott, Donald R. et al., "Off-Axis Paths in Spherical Mirror Interferometers", Applied Optics, 3(4): 523-526 (1964).

"In-Situ Sensors for the Chemical Industry—Final Report", project report of "Development of In Situ Analysis for the Chemical Industry", the Dow Chemical Company, Principle investigator: Dr. J.D. Tate, profect No. DE-FC36-o21D14428, pp. 1-37, Jun. 30, 2006.

Kessler, William J. et al.,"Near-IR diode laser-based sensor for pb-level water vapor in industrial gases", Proceedings of the SPIE, 3537: 139-149 (1999).

May, Randy D. et al., "Data Processing and Calibration for Tunable Diode Laser Harmonic Absorption Spectrometers", Journal of Quantitative Spectroscopy and Radiative Transfer, 49(4): 335-347 (1993).

May, Randy D. et al., "Open-Path, Near-Infrared Tunable Diode Laser Spectrometer for Atmospheric Measurements of $H_2O$", Journal of Geophysical Research, 103:19161-19172 (1998).

May, Randy D., "Computer Processing of Tunable Diode Laser Spectra", Applied Spectroscopy, 43(5): 834-839 (1989).

May, Randy D., "Next-Generation Diode Laser Gas Sensors for Environmental and Industrial Monitoring", Proceedings of the SPIE, 3858: 110-118 (1999).

Paige, Mark E., "Commercial Gas Sensing with Vertical Cavity Lasers", Advanced Semiconductor Lasers and Their Applications Conference Technical Digest; pp. 141-143 (1999).

Philippe, Louis C. et al., "Laser diode wavelength-modulation spectroscopy for simultaneous measurement of temperature, pressure, and velocity in shock-heated oxygen flows", Applied Optics, 32(30): 6090-6103 (1993).

Reid, J. et al., "Second-Harmonic Detection with Tunable Diode Lasers—Comparison of Experiment and Theory", Applied Physics, B 26: 203-210 (1981).

Richter, Dirk et al., "Development of an automated diode-laser-based multicomponent gas sensor", Applied Optics, 39(24): 4444-4450 (2000).

Rothman et al., "The HITRAN molecular spectroscopic database: edition of 2000 including updates through 2001", Journal of Quantitative Spectroscopy & Radiative Transfer, 82: 5-44 (2003).

Scott, David C. "Airborne Laser Infrared Absorption Spectrometer (ALIAS-II) for in situ atmospheric measurements of $N_2O$, $CH_4$, CO, HCL and $NO_2$ from balloon or remotely piloted aircraft platforms", Applied Optics, 38(21): 4609-4622 (1999).

Silver, Joel A., "Frequency-modulation spectroscopy for trace species detection: theory and comparison among experimental methods", Applied Optics, 31(6): 707-717 (1992).

Wang, Jian et al., "In situ combustion measurements of CO with diode-laser absorption near 2.3 μm", Applied Optics, 39(30): 5579-5589 (2000).

Webster, Christopher R. et al., Aircraft (ER-2_laser infrared absorption spectrometer (ALIAS) for in-situ stratospheric measurements of HCL $N_2O$, $CH_4$, $NO_2$, and $HNO_3$, Applied Optics, 33(3): 454-472 (1994).

Webster, Christopher R. et al., "Quantum-cascade laser measurements of stratospheric methane and nitrous oxide", Applied Optics, 40(3): 321-326 (2001).

Webster, Christopher R. et al., "Tunable diode laster IR spectrometer for in situ measurements of the gas phase composition and particle size distribution of Titan's atmosphere", Applied Optics, 29(7): 907-917 (1990).

Zhou, Xin et al., "Development of a sensor for temperature and water concentration in combustion gases using a single tunable diode laser", Measurement Science and Technology, 14: 1459-1468 (2003).

'The HITRAN Database', [online]. Harvard-Smithsonian Center for Astrophysics, 2006, [retrieved on May 8, 2007]. Retrieved from the Internet: <URL: www.cf.harvard.edu/hitran/welcometop.html>.

Arroyo et al., "Absorption Measurements of Water-Vapor Concentration, Temperature, and Line-Shape Parameters Using a Tunable InGaAsP Diode Laser", Applied Optics, 32(30): pp. 6104-6116 (Oct. 20, 1993).

Allen, Mark G.,"Diode laser absorption sensors for gas-dynamic and combustion flows", Meas. Sci. Technol.; 9:545-562 (1998).

Arroyo, et al., "Absorption Measurements of Water-Vapor Concentration, Temperature, and Line-Shape Parameters Using a Tunable INGAASP Diode Laser", Applied Optics, 32(30): 6104-6116 (Oct. 20, 1993).

Liu, Xiang, "Line-of-Sight Absorption of $H_2O$ Vapor: Gas Temperature Sensing in Uniform and Nonunimorm Flows"; Submitted to the Department of Mechanical Engineering and the Committee on Graduate Studies, in Partial Fulfillment of the Requirements for the Degree of Doctor of Philosophy, Stanford University, Jun. 2006.

May, Randy D. et al., "The MVACS tunable diode laser spectrometers", Journal of Geophysical Research, 106(E8): 17673-17682 (Aug. 25, 2001).

May, Randy D., "Correlation-based technique for automated tunable diode laser scan stabilization", Rev. Sci. Instrum.; 63(5): 2922-2926 (1992).

Silver, Joel A. et al.,"Diode laser measurements of concentration and temperature in microgravity combustion", Meas. Sci. Technol, 10:845-852 (1999).

Varga, A. et al., "Photoacoustic system for on-line process monitoring of hydrogen sulfide ($H_2S$) concentration in natural gas streams", Applied Physics B, 85: 315-321 (2006).

Webster, Christopher R. et al., "Simultaneous in Situ Measurements and Diurnal Variations of NO, $NO_2$, $O_3$,/$NO_2$, $CH_4$, $H_2O$, and $CO_2$ in the 40- to 26-km Region Using an Open Path Tunable Diode Laser Spectrometer", Journal of Geophysical Research, 92(D10): 11931-11950 (Oct. 20, 1987).

International Search Report for related patent PCT/US2007/009648 performed by International Searching Authority/EP on Sep. 20, 2007.

Written Opinion of the International Searching Authority for related patent PCT/US2007/009648 performed by International Searching Authority/EP on Sep. 20, 2007.

U.S. Appl. No. 10/688,723, filed Oct. 16, 2003, Randy May.

International Search Report and Written Opinion dated Aug. 6, 2008, issued in connection with related international patent application PCT/US2008/060128.

Weldon, V., et al., "H2S and C02 gas sensing using DFB laser diodes emitting at 1.57µm," Sensors and Actuators B, Elsevier Sequoia S.A., Lausanne, CH, vol. 29, No. 11 Oct. 1995, pp. 101-107.

* cited by examiner

MEASURING WATER VAPOR IN HYDROCARBONS

RELATED APPLICATIONS

The present patent application claims priority under 35 U.S.C. §119 to U.S. Provisional Patent Application Ser. No. 60/793,404, filed on Apr. 19, 2006, and entitled "MEASUREMENT OF MOISTURE IN OLEFIN GASES", the entire disclosure of which is incorporated by reference herein.

TECHNICAL FIELD

The subject matter disclosed herein relates to measurements of water vapor concentrations in hydrocarbon gas mixtures.

BACKGROUND

Currently available techniques for characterizing water vapor in hydrocarbon gas mixtures suffer from various drawbacks. For example, maintenance and calibration issues in the field may make their use cumbersome and costly. In addition, these techniques may be difficult to calibrate, may drift over time, and may generally fail to provide rapid response and recovery times.

One conventional technique measures the dew point of the water vapor in a gas mixture by flowing the gas mixture over a chilled mirror. Moisture in the sampled gas mixture condenses on the mirror when the mirror's temperature is at or below the dew point of the gas mixture. To estimate the water vapor concentration, the temperature of the mirror is scanned through an appropriate range from warmer to cooler, and the temperature is measured when condensation begins on the mirror surface. The dew point is a function of the relative humidity of the gas mixture, which is readily converted to a partial pressure or concentration of water vapor in the gas mixture. Detection of condensation on the mirror may be accomplished visually or by optical means. For example, a light source may be reflected off the mirror into a detector and condensation detected by changes in light reflected from the mirror. The observation may also be done by eye. However, the exact point at which condensation begins is often not readily distinguishable in this manner. Also, because the mirror temperature passes dynamically through the dew point, the error in the measurement tends to be substantial. Other, lower vapor pressure components of the gas mixture, such as higher molecular weight hydrocarbons, alcohols, and glycols, may also condense on the mirror as it cools. Automated on-line systems may be unable to distinguish between gas mixture components that condense on the mirror surface, and manual systems generally require highly skilled operators.

Another conventional technique uses two closely spaced, parallel windings coated with a thin film of phosphorous pentoxide ($P_2O_5$). An electrical potential applied to the windings electrolyzes water molecules adsorbed by the coatings to hydrogen and oxygen. The current consumed by the electrolysis reaction is proportional to the mass of water vapor entering the sensor. The flow rate and pressure of the incoming sample must be controlled precisely to maintain a standard sample mass flow rate into the sensor. However, contamination from oils, liquids or glycols on the windings causes drift in the readings and may damage the sensor. The sensor reacts slowly to sudden changes in moisture, as the absorption reaction on the surfaces of the windings takes some time to equilibrate. Large amounts of water in a gas mixture (commonly known as "slugs") may wet the surface which requires tens of minutes or hours to "dry-down" before accurate measurements are again possible. As such, effective sample conditioning and removal of liquids is essential when using this sensor.

Still another conventional technique utilizes piezoelectric adsorption. Such an instrument compares changes in the frequency of hygroscopically coated quartz oscillators. As the mass of the crystal changes due to adsorption of water vapor on the hygroscopic coating, the resonant frequency of the quartz crystal changes. The sensor is a relative measurement that requires an integrated calibration system with desiccant dryers, permeation tubes and sample line switching. These instruments may also suffer from interference by glycol, methanol, and other polar molecules as well as from damage from hydrogen sulfide. However, the required calibration system is not as precise and adds to the cost and mechanical complexity of the system. Labor for frequent replacement of desiccant dryers, permeation components, and the sensor heads greatly increase operational costs. Additionally, as with the electrolysis-based system described above, slugs of water may render the system nonfunctional for long periods of time as the sensor head "dries-down."

Aluminum and silicon oxide sensors have also been used. These sensors include an inert substrate material and two dielectric layers, one of which is sensitive to humidity. Water molecules in the gas mixture pass thru pores on an exposed surface of the sensor and cause a change to a physical property of the layer beneath it. In an aluminum oxide sensor, two metal layers form the electrodes of a capacitor. The dielectric constant of the sensor changes as water molecules adsorb to its surface. The sensor impedance is correlated to the water concentration. A silicon oxide sensor is an optical device whose refractive index changes as water is absorbed into the sensitive layer. When light is reflected through the substrate, a wavelength shift can be detected on the output which can be precisely correlated to the moisture concentration.

With aluminum and silicon oxide sensors, water molecules take time to enter and exit the pores so some wet-up and dry down delays will be observed, especially after a slug. Contaminants and corrosives may damage and clog the pores causing a "drift" in the calibration. As with piezoelectric and electrolytic sensors, these sensors are susceptible to interference from glycol, methanol, and other polar organic compounds. The calibration may drift as the sensor's surface becomes inactive due to damage or blockage, so the calibration is most reliable at the beginning of the sensor's life.

SUMMARY

In a first aspect, a first sample of an olefin gas mixture is dehydrated to reduce its water vapor concentration, and a first absorption spectrum is recorded for the first sample at a chosen wavelength. A second absorption spectrum is recorded for a second sample of the olefin gas mixture at the chosen wavelength, and a differential absorption spectrum is generated from the first absorption spectrum and the second absorption spectrum. The differential spectrum is analyzed to determine a concentration of water vapor in the olefin gas mixture.

In various optional aspects, the first and second absorption spectra may be recorded using a harmonic spectroscopy method, a direct absorption spectroscopy method, a single line absorption peak spectroscopy method, or a multiple line absorption peak spectroscopy method. The first absorption spectrum may optionally be recorded by illuminating the first sample with light at a chosen wavelength, measuring a first transmitted intensity of light passing through the first sample, and passing the measured intensity to a data analysis device while the second absorption spectrum may be recorded by illuminating the second sample with light at the chosen wavelength, measuring a second transmitted intensity of light passing through the second sample, and passing the measured intensity to the data analysis device. The first absorption spectrum and the second absorption spectrum may be recorded sequentially in a single sample cell. Alternatively, the first absorption spectrum and the second absorption spectrum may be recorded in parallel in first and second sample cells with substantially identical optical path lengths.

In a second interrelated aspect, an apparatus may include a laser light source that emits at a chosen wavelength, a sample cell, a dehydrator that reduces water vapor in a first sample of an olefin gas mixture, one or more valves for alternatively providing the first sample or a second sample of the olefin gas mixture to the sample cell, and a photodetector positioned to quantify light passing through the sample cell. A microprocessor that records a first absorption spectrum from the photodetector when the sample cell contains the first sample, records a second absorption spectrum when the sample cell contains the second sample, calculates a differential absorption spectrum from the first and second absorption spectra, and calculates a concentration of water vapor in second sample based on the differential absorption spectrum is also included.

In a third interrelated aspect, an apparatus may include a laser light source that emits at a chosen wavelength, a dehydrator to reduce water vapor in a first sample of an olefin gas mixture, a first sample cell for containing the first sample, and a second sample cell for containing a second sample of the olefin gas mixture. The second sample cell has a substantially identical path length to the first sample cell. Optical components for splitting the beam between the first sample cell and the second sample cell are also included. A first photodetector is positioned to quantify light passing through the first sample cell, and a second photodetector is positioned to quantify light passing through the second sample cell. A microprocessor records a first absorption spectrum from the first photodetector, records a second absorption spectrum from the second photodetector, calculates a differential absorption spectrum from the first and second absorption spectra, and calculates the concentration of water vapor in second sample based on the differential absorption spectrum.

In various optional aspects, the laser light source may be a tunable diode laser. The laser light source may also be modulated and the first and the second absorption spectra may be harmonic absorption spectra, direct absorption spectra, or multiple line absorption spectra. The laser light source may optionally a vertical cavity surface emitting laser, a horizontal cavity surface emitting laser, a quantum cascade laser, a distributed feedback laser, or a color center laser. The chosen wavelength may be one that is absorbed at least approximately 0.001 times as strongly by air with a concentration of 100 ppm of water vapor as by dry air containing an olefin concentration approximately equivalent to that in the olefin gas mixture. The chosen wavelength may optionally be selected from 1359.5 nm, 1856.7 nm, 2605.6 nm, 1361.7 nm, 1859.8 nm, 2620.5 nm, 1368.6 nm, 1877.1 nm, 2626.7 nm, 1371.0 nm, 1890.3 nm, 2630.6 nm, 1392.2 nm, 1899.7 nm, 2665.1 nm, 1836.3 nm, 1903.0 nm, 2676.1 nm, 1840.0 nm, 1905.4 nm, 2711.2 nm, 1842.1 nm, 2573.6 mm, 2724.2 nm, 1847.1 nm, 2583.9 nm, 2735.0 mm, 1854.0 nm, 2596.0 nm, and 2740.3 nm. A thermally controlled chamber that encloses one or more of the laser source, the photodetector, and the sample cell or cells may also be included, as may an additional water vapor concentration analyzer such as a dew point measurement device, a piezoelectric adsorption device, a phosphorus pentoxide electrolysis device, or an aluminum or silicon oxide sensor.

DESCRIPTION OF THE DRAWINGS

This disclosure may be better understood upon reading the detailed description and by reference to the attached drawings, in which.

DETAILED DESCRIPTION

Figure 1:
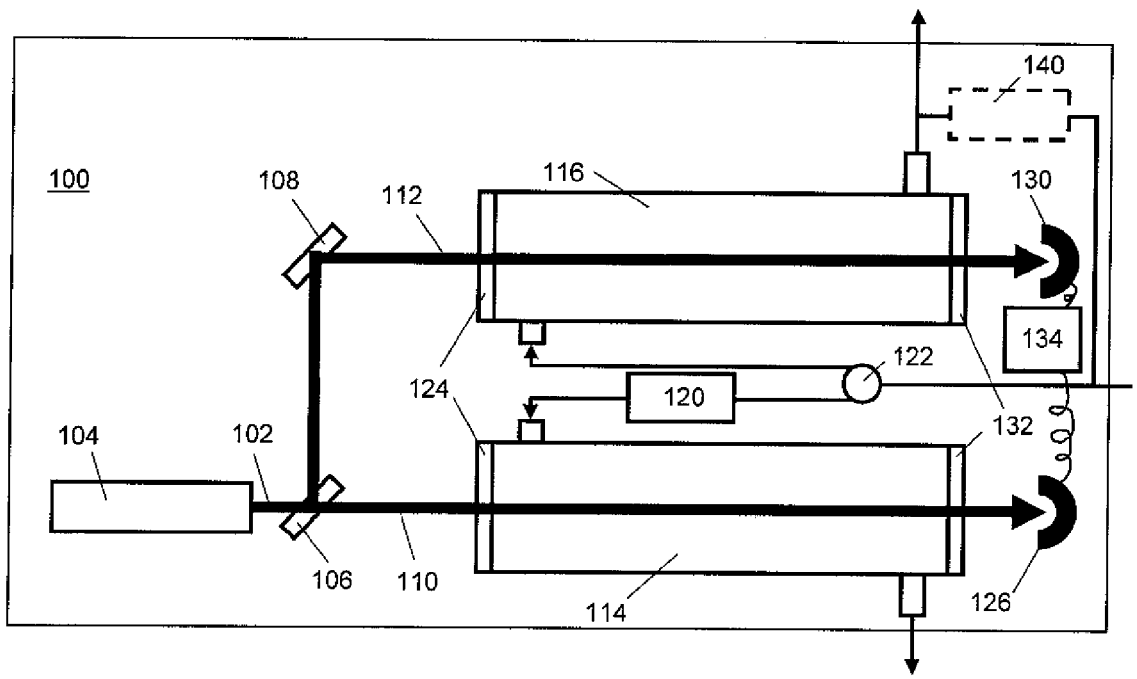
FIG. 1 is a schematic diagram showing a first example of an absorption spectrometer.

Alkenes are unsaturated, open chain hydrocarbons with a single carbon-carbon double bond that have the general formula $C_nH_{2n}$. In the petrochemical industry, the term "olefins" is often used generically to describe compounds including, but not limited, ethylene, propylene, and isobutane. Among other uses, these compounds serve as feed stocks for the petrochemical industry. Many petrochemical processes are quite sensitive to the presence of contaminants, such as water, in feed gases provided to the reactors. As such, measurement of water vapor in feed gas streams of these olefins is of particular interest to the industry.

Low levels of trace gases in gas mixtures may be measured using absorption spectroscopy. A light beam of suitable wavelength is passed through a sample of a gas that is contained within a sample cell. As light passes through the gas, some of its intensity is absorbed by trace gas molecules that absorb at that specific wavelength. The amount of light absorbed is dependent on the concentration (partial pressure) of gas and can therefore used as a measure of the concentration. This arrangement is suitable when the background gas has no or very weak absorption features in the spectral region being used for the trace gas measurement.

Spectroscopic methods are not limited to mixtures of a trace gas in a pure background gas, however. A differential absorption spectrum may be generated by recording an absorption spectrum of the background gas and subtracting it from the spectrum of the mixture (trace gas plus background gas). This measurement yields the absorption spectrum of the trace gas for mixtures where the background gas has interfering absorption features which are not strong enough to completely absorb the laser light. However, this technique is not effective under saturated absorption conditions.

Near infrared radiation generally lacks sufficient photon energy to induce absorption by electronic transitions such as those induced by ultraviolet radiation. Therefore, IR absorption is restricted to compounds with small energy differences in the possible vibrational and rotational states of the molecules. For a molecule to absorb IR radiation, the vibrations or rotations within a molecule must cause a net change in the dipole moment of the molecule. The alternating electrical field of the radiation interacts with fluctuations in the dipole moment of the molecule. The energy of the incident light radiation is $$E = h\nu \quad (1)$$

where E is the photon energy, h is Planck's constant and $\nu$ is the frequency of the light. If E matches the energy necessary to excite a vibrational mode of a molecule, then radiation will be absorbed causing a change in the amplitude of this molecular vibration. The two main types of molecular motion, which includes relative motion between atoms making up the molecule, involve stretching and vibration of inter-atomic bonds.

Stretching transitions require moderate energies and are therefore quite useful to IR absorption spectroscopy. In stretching transitions, the inter-atomic distance changes along bond axes, and the resultant absorbance of IR by gas-phase molecules yield line spectra sufficiently spaced apart to allow detection. In liquids or solids, these lines broaden into a continuum due to molecular collisions and other interactions such that they cannot be measured by IR absorption spectroscopy.

The relative positions of atoms in molecules are not fixed, but are rather subject to a number of different vibrations relative to other atoms in the molecule. A specific molecular motion requires a corresponding quantum of activating photon energy. Therefore, an incident photon's energy must be of exactly the right wavelength to be absorbed into the molecule. Thus, if a gas containing a molecule that absorbs and vibrates at a given wavelength $\lambda$ is illuminated by a beam of light of wavelength $\lambda$, some of the incident photons will be absorbed as it passes through the gas. This absorbance $A_{i,\lambda}$ is calculated from the beam power incident on the sample $P_0$ and the beam power passing through the sample P as follows:

$$A_{i,\lambda} = -\ln(P/P_0) \quad (2)$$

In accordance with Beer-Lambert's Law, the absorbance $A_{i,\lambda}$ due to a specific gas-phase compound i at the incident wavelength $\lambda$ is directly proportional to its concentration $C_i$ in the cell:

$$A_{i,\lambda} = C_i \epsilon_{i,\lambda} L \quad (3)$$

where $\epsilon_{i,\lambda}$ is the extinction coefficient for the compound at the incident wavelength, and L is the path length of the absorption/sample cell. If multiple compounds in the sample cell absorb light at the incident wavelength $\lambda$, the total absorbance $A_{T,\lambda}$ of the gas mixture in the cell at that wavelength is $$A_{T,\lambda} = L \sum_{i=1}^{n} C_i \epsilon_{i,\lambda} \quad (4)$$

As such, the absorbance $A_{i,\lambda}$ of a single compound at the incident wavelength may be extracted from $A_{T,\lambda}$ as follows:

$$A_{i,\lambda} = A_{T,\lambda} - A_{T-I,\lambda} \quad (5)$$

where $A_{T-I,\lambda}$ is the absorbance of the gas mixture with compound i removed.

An analyzer used in connection with the subject matter disclosed here may be used to make measurements of any number of trace gases in other gases or mixtures of gases. The system includes a source of incident light, such as a laser, one or more detectors with sensitivity in the wavelength range of the light source, and one or more absorption cells, each arranged such that the gas provides a path length L though which a beam from the light source passes before reaching the detector. Control electronics, such as a microprocessor, and user accessible input/output channels may also be included. The following is a general description of various examples of such devices and their operation.

Figure 2:
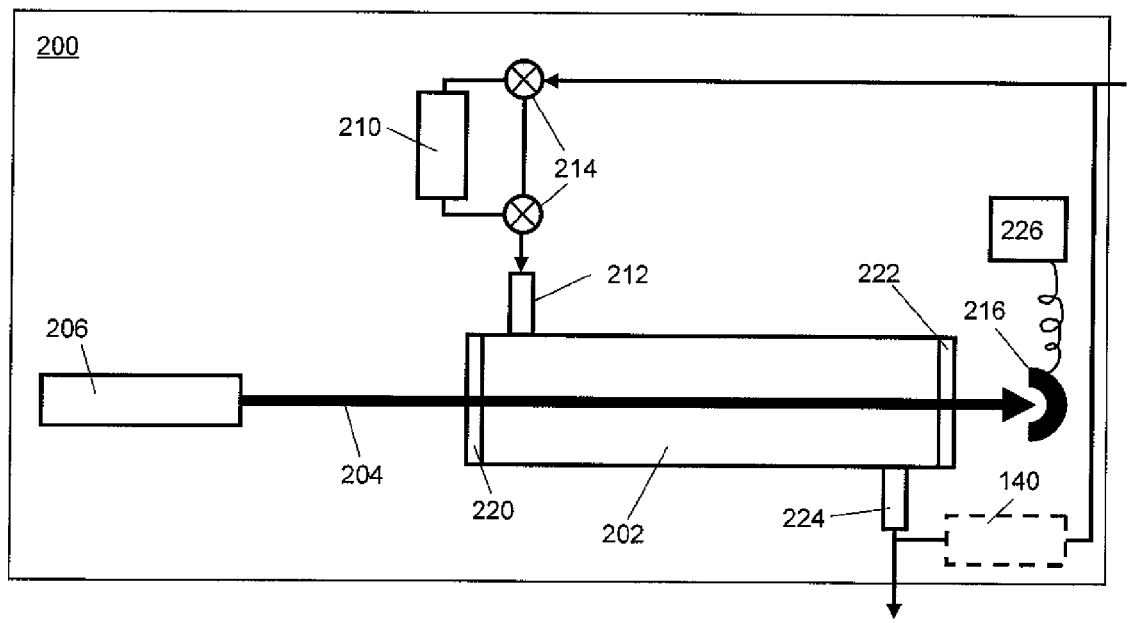
FIG. 2 is a schematic diagram showing a second example of an absorption spectrometer.

Two illustrative implementations of the analyzers disclosed here are depicted in FIG. 1 and FIG. 2. FIG. 1 depicts an analyzer 100 with a dual beam arrangement in which the beam 102 from the light source 104 is split by a beam splitter 106 and mirror 108 into a first beam 110 and a second beam 112 that passes through gas held in a first 114 and a second 116 sample cell, respectively. The first sample cell 114 contains a first sample of gas that is treated to be a background or reference sample. The background or reference sample is prepared by treating the first sample of the gas of interest to reduce the water vapor concentration as described in more detail below. The second sample cell 116 contains a second sample of the gas that has not been dehydrated, dehumidified, or the like. FIG. 2 shows an alternative detector 200 with a single beam, single sample cell arrangement in which the first sample and the second sample alternatively and sequentially enter the sample cell 202 where they are illuminated by the beam 204 from the light source 206.

More specifically, with reference to the analyzer 100 shown in FIG. 1, the first beam 110 is directed through the first sample cell 114 containing the first sample which has been dehydrated by passing it through a dehydrator 120. The second beam 112 is directed through a second sample cell 116 of identical optical path length to the first sample cell 114. The second sample cell 116 contains the second sample which has not been dehydrated. As such, the second sample contains components found in the first sample (e.g. the background or reference sample) in addition to water vapor at the concentration present in the gas being measured. In operation, gas flowing into the detector is split between the two first 114 and the second 116 sample cells. This may be accomplished by a flow divider 122 or other equivalent apparatus for dividing gas flow between two channels. Gas flowing to the second sample cell 116 passes through the dehydrator 120 that reduces the water vapor concentration from the gas mixture to produce the first sample that is the background or reference sample. The dehydrator 120 may be any device or process that reduces the concentration of water vapor in a gas, including but not limited to a molecular sieve, a chemical scrubber, a getter, a filter or trap that is selective for water molecules, a gas separating membrane, a condenser, or the like. The dehydrator 120 is advantageously chosen to not substantially affect the concentration of the other components of the sample gas mixture. Gas flowing to the second sample cell 116 does not pass through the dehydrator 120.

The split beams 110 and 112 pass into the first 114 and second 116 sample cells respectively. Depending on the configuration of the analyzer 100, the incident light may pass through first windows 124 as shown in FIG. 1. The gas in each sample cell may absorb some fraction of the beam intensity, and the first and second light beams 110 and 112 then impinge upon a first 126 and a second 130 photodetector, respectively. Depending on the configuration the beams may pass through second windows 132 to exit the first and second sample cells. The example illustrated in FIG. 1 depicts the first and second sample cells as single pass configurations in which the beams enter the respective sample cells through first windows 124, pass through the gas contained in each sample cell, and exit the respective sample cells through second windows 132. Other configurations are within the scope of the disclosure, as discussed below.

The first photodetector 126 quantifies the intensity of the first beam impinging upon it, and thus passing through the first sample cell 114, as a function of wavelength. Likewise, the second photodetector 130 quantifies the intensity of the second beam impinging upon it, and thus passing through the second sample cell 116, as a function of wavelength. In this manner, the first photodetector 126 quantifies the transmitted intensity for the first sample, in this example the dehydrated background or reference gas, and the second photodetector 130 quantifies the transmitted intensity for the second sample, which has not been dehydrated. Data from the first photodetector 126 and the second photodetector 130 are passed to a data analysis device 134, such as for example a microprocessor, which records and/or processes data from the photodetector to generate a differential spectrum from which the water vapor concentration in the second sample may be calculated. The concentration of water vapor is dependent on the mole fraction of water molecules as well as the temperature and pressure of the gas being measured. As such, the temperature and pressure in the first 114 and second 116 sample cells may be monitored and/or controlled.

To account for detector drift and other potential measurement artifacts, some variations may periodically record an absorption spectrum for each sample cell with no gas to determine the photodetector's dark current "zero" or to periodically reverse the flows such that the first sample cell 114 is supplied with undehydrated gas and the second sample cell is supplied with the dehydrated, background gas sample.

FIG. 2 depicts an analyzer 200 with a single-beam arrangement. A first sample that has been dehydrated to reduce its water vapor concentration and a second, undehydrated sample are alternately illuminated by the beam 204 from the light source 206 in a sample cell 202. Spectra are recorded individually for the first sample, which is the dehydrated background or reference sample, and the second sample, which is not dehydrated. For a flow system, this process may be performed continuously and sequentially. The analyzer 200 in FIG. 2 includes a dehydrator 210 that may be placed in series with the gas inlet 212 to the sample cell 202 by, for example a pair of 2-way valves 214 which may optionally be solenoid valves. As noted above, the dehydrator 210 may be any device or process that reduces the concentration of water vapor in a gas, including but not limited to a molecular sieve, a chemical scrubber, a getter, a filter or trap that is selective for water molecules, a gas separating membrane, a condenser, or the like. The dehydrator 210 is advantageously chosen to not substantially affect the concentration of the other components of the sample gas mixture. The second sample is not passed through the dehydrator 210 and as such retains the water vapor concentration that is present in the gas being measured.

In operation of the analyzer 200 shown in FIG. 2, gas is alternatively conveyed to the sample cell inlet 212 either directly or via the dehydrator 210 by appropriate operation of the two way valves 214. The photodetector 216 quantifies the intensity of the beam 204 impinging upon it, and thus passing through the sample cell 202, as a function of wavelength. Thus, when the first sample, which passes through the dehydrator to reduce its water vapor concentration, is in the sample cell 202 the photodetector 216 quantifies the transmitted intensity for the first sample, in this example the dehydrated background or reference gas. The photodetector 216 quantifies the transmitted intensity for the second sample, containing the original water vapor concentration, when gas flows directly to the sample cell without passing through the dehydrator 210.

The sample beam may optionally enter the sample cell through an input window 220 and exit the cell though an exit window 222. Alternative sample cell configurations, such as those discussed above in regards to FIG. 1, are also within the scope of this disclosure. Gas exits the sample cell 202 via the exhaust outlet 224. Intensity data from the photodetector 216 are passed to a data analysis device 226, such as for example a microprocessor. The data analysis device 226 records and/or processes data received from the photodetector for the first sample and the second sample to generate a differential spectrum from which the water vapor concentration in the second sample may be calculated. The concentration of water vapor is dependent on the mole fraction of water molecules as well as the temperature and pressure of the gas being measured. As such, the temperature and pressure in the sample cell 202 may be monitored and/or controlled.

As noted above, a first sample and a second, dehydrated sample of a gas are illuminated by a laser light source. The path length of the sample cell may be varied depending on the strength of the specific absorption line of interest or the magnitude of the difference between the absorption line of interest and interfering absorption lines from other gas species present. A cell of insufficient length may not provide sufficient sensitivity while one of excessive length may absorb the entirety of the incident light such that no measurable signal reaches the detector (a situation called saturation). A usable range of sample cell path lengths may be determined using equation 3 and the expected concentrations of absorbing gases in the sample cell and the extinction coefficients of those gases.

In some cases, the concentration of water vapor in the olefin gas mixture may be very small or not readily distinguishable from other components present in the gas. In such cases, the length of the cell may be increased to increase the sensitivity of the measurement. As equation 3 states, $A_{i,\square}$ is directly proportional to the path length L over which the laser beam traverses the olefin gas mixture. Thus, a cell that is twice as long will absorb twice as much light etc. Therefore, in some implementations of the analyzers described here, sample cells are employed that have path lengths on the order of many meters or even thousands of meters.

To achieve longer optical path lengths without the use of extremely long sample cells, sample cell configurations within the scope of this disclosure may also include the use of one or more mirrors to reflect the beam such that the beam passes through the sample contained in the sample cell two or more times. In such a multipass configuration, the beam may enter and exit the cell through the same window or through different windows. In some implementations, windowless sample cell configurations may be utilized in which, for example, the laser source and/or the photodetector are contained within the sample cell.

Figure 3:
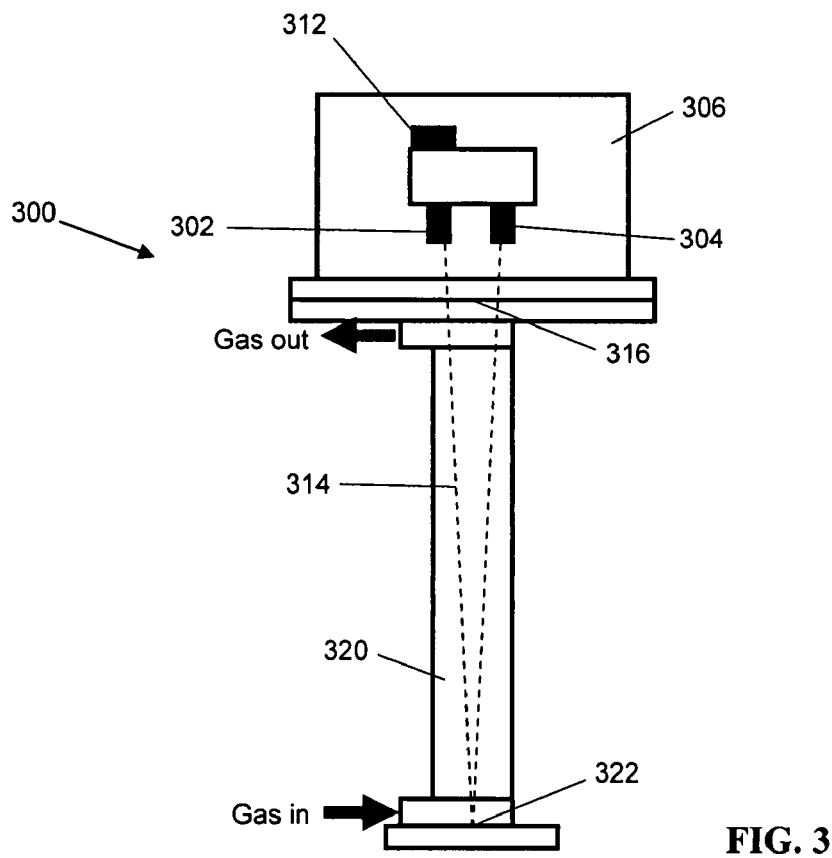
FIG. 3 is a schematic diagram showing a third example of an absorption spectrometer.

One example of such a multipass sample cell configuration is shown in FIG. 3, which depicts a two-pass absorption cell and laser/detector head 300. A laser 302 and photodetector 304 are positioned in an optical head 306 mounted to a baseplate 310 whose temperature is controlled by a thermoelectric cooler (TEC) 312. The incident laser light 314 is directed out of the optical head 306 through a window 316 into the sample cell 320. The light travels the length of the sample cell 320 twice as it is reflected at the far end of the cell by a flat mirror 322. The returning light is transmitted back through the window 316 and impinges on the photodetector 304. The analyzers shown in FIG. 1 and FIG. 2 may be modified to incorporate a multipass detector head as shown in FIG. 3.

Figure 4:
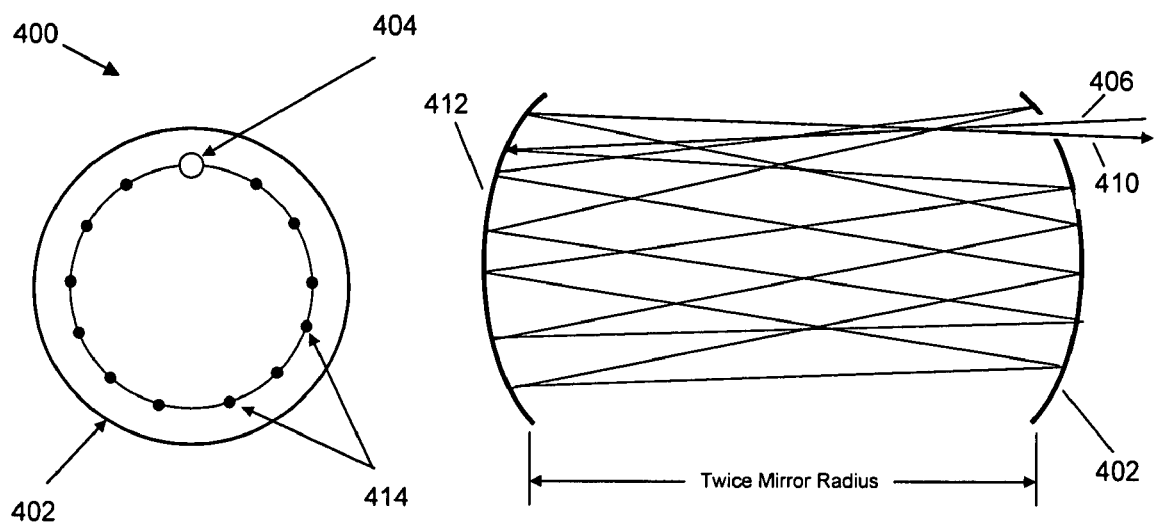
FIG. 4 is a schematic diagram that illustrates concepts associated with a Herriott cell.

Another way to achieve longer path lengths is through the use of the "Herriott" cell, or off-axis resonating cavity. In such a system, long optical paths are physically compact by reflecting the beam repeatedly without interference between adjacent beams as shown the schematic diagrams 400 in FIG. 4. The Herriott cell comprises two spherical mirrors spaced at a distance that enables a certain number of reflections of the laser beam before it meets the re-entrant condition and goes out of the cell cavity through the beam injection hole. With a Herriott cell, long optical paths can be achieved physically compact by reflecting the beam repeatedly without interference between adjacent beams. Depending on the desired sensitivity, the number of reflections of the Herriott cell can be adjusted by changing the spacing of the two mirrors or by using different mirrors with different focal lengths.

Such long effective path lengths may also be achieved by using an off-axis resonating cavity which includes two highly reflective mirrors. These cells are variants of cavity ring down spectrometers that are called integrated cavity output spectrometers (ICOS). These long cells may also be used to make these very sensitive measurements using either direct absorption or "2f" detection. The front view of one such mirror 402 shows an input/output aperture 404 for allowing the light beam to enter 406 the cell and then exit 410 the cell on the way to the photodetector (not shown). The opposite mirror in such a cell 412 in this cell does not have an aperture. An alternative configuration of a Herriot Cell includes an aperture in each of the facing mirrors such that the beam enters through an aperture in one mirror and exits the cell through an aperture in the other mirror. The end mirror 402 shown in FIG. 4 also illustrates how the laser beam contact points 414 on the mirror 402 are arranged in a circle such that the beam does not interfere with itself as it is relayed back and forth between two such mirrors.

Herriott Cells may be designed for a broad number of cell lengths but tend to have an upper bound that depends on the reflectance of the mirrors. If the reflectance of the mirrors at the operating wavelength is not very high, the incident light beam rapidly loses intensity as it traverses back and forth between the mirrors. For example, for a mirror reflectance of 98%, the intensity of light reaching the photodetector after 70 passes is $0.98^{70}$ or only 24.3% of that when the beam enters the cell. If this light is further attenuated by absorption by gas molecules in the cell, the amount actually reaching the photodetector may be quite small.

Additional information about Herriot cells and general background information on their use in absorption spectroscopy may be found in the following references, each of which is incorporated by reference in its entirety: D. Herriott, H. Kogelnik and R. Kompfner, "Off Axis Paths in Spherical Mirror Interferometers," *Applied Optics*, Vol. 3, No. 4, 1964; Donald R. Herriott and Harry J. Schulte, "Folded Optical Delay Lines," Applied Optics, Vol. 4, No. 8, 1965; Alphan Sennaroglu and James G. Fugimoto, "Design Criteria for Herriott-type Multi-pass Cavities for Ultrashort Pulse Lasers," *Optics Express*, vol. 11, No. 9, 2003; and Jean Francois Doussin, Ritz Dominique and Carlier Patrick, "Multiple-pass Cell for Very-long-path Infrared Spectrometry," *Applied Optics*, Vol. 38, No. 19, 1999.

The light source used for the absorption measurements disclosed may emit in the infrared (for example in a wavelength range of approximately 800 to 10,000 nm). The analyzer may utilize a laser whose spectral bandwidth is much narrower than the bandwidth of the absorption lines of interest. Such an arrangement allows for single line absorption spectroscopy in which it is not necessary to scan the entire width of the absorption line or even the peak absorption feature of the line. The wavelength of the laser may be chosen to be one at which there is a resolvable difference in the relative absorbance of water molecules and the other components of the gas to be measured. In one implementation, the laser frequency may be scanned (tuned) back and forth across the chosen absorption wavelength while a photodetector positioned at the opposite end of the beam path length quantifies the light intensity transmitted through the sample as a function of wavelength.

A tunable diode laser TDL may be employed as the laser source for the disclosed analyzers. Examples of tunable lasers that may be used are the distributed feedback laser (DFB), the vertical cavity surface emitting laser (VCSEL), and the horizontal cavity surface emitting laser (HCSEL). These lasers can be direct emitters or fiber coupled. Quantum cascade lasers may also be utilized as can other lasers capable of producing a beam of incident light in the desired wavelength range.

DFB Lasers employ a distributed Bragg grating etched onto the active layer of a semiconductor laser which locks the central wavelength within the gain band. As such, only a single longitudinal mode is pumped from the available energy. This optical structure is sensitive to refractive index variations due to carrier density (more or less proportional to the current applied at the junction) and temperature. When laser current and laser temperature are accurately controlled, the peak wavelength can be tuned accurately along a useful range. The control using current is fast, but the sensitivity to the central frequency is weak, typically on the order of 0.01 nm/mA. This sensitivity is weak for large tuning distances, but is strong enough to obtain a flat output power while tuning wavelength by changing the temperature. Thermal stabilization time for a standard DFB module is relatively slow, on the order of a few seconds, which makes this type of controlled source more appropriate for fixed temperature, controlled current applications.

A VCSEL is a type of semiconductor laser diode whose laser beam is emitted perpendicular to the wafer chip surface, in contrast to conventional edge-emitting semiconductor lasers which emit from surfaces formed by cleaving the individual chip out of a wafer. The laser resonator includes two distributed Bragg reflector (DBR) mirrors parallel to the wafer surface with an active region consisting of one or more quantum wells for the laser light generation in between. The planar DBR-mirrors consist of layers with alternating high and low refractive indices. Each layer has a thickness of a quarter of the laser wavelength in the material, yielding an intensity reflectivity above 99%. High reflectivity mirrors are required in VCSELs to balance the short axial length of the gain region. In some VCSELs the upper and lower mirrors are doped as p-type and n-type materials, forming a diode junction. In more complex structures, the p-type and n-type regions may be buried between the mirrors, requiring a more complex semiconductor process to make electrical contact to the active region, but eliminating electrical power loss in the DBR structure. VCSELs for wavelengths from 650 nm to 1300 nm are typically based on gallium arsenide (GaAs) wafers with DBRs formed from GaAs and aluminum gallium arsenide. Longer wavelength devices, from 1300 nm to 2000 nm, have been made with at least the active region made of indium phosphide.

A horizontal-cavity surface-emitting laser (HCSEL) combines the power and high reliability of an edge-emitting laser with the low cost and ease of packaging of a vertical cavity surface-emitting laser (VCSEL). The HCSEL is a semiconductor laser with an elongated cavity that is fabricated on a substrate by etching a 45° angled facet at the emitter end and a 90° facet at the back end of the cavity. The rear reflective region can incorporate an etched distributed Bragg reflector next to the rear facet. Dielectric coatings may be used for reflectivity control.

Quantum Cascade Lasers (QCL) are semiconductor lasers that rely on transitions within several quantum wells that normally emit in the mid-infrared spectral region. QCLs operate on laser transitions not between different electronic bands but on intra quantum well transitions of a semiconductor structure. By using a multitude of quantum wells in a series, a higher optical gain is achieved. Transition energies are defined not by fixed material properties but rather by design parameters (particularly by layer thickness values of quantum wells). As such, QCLs can be designed for operational wavelengths ranging from a few microns to well above 10 microns. High efficiencies may be achieved using a cascade of laser transitions, where a single electron can generate dozens of mid-infrared photons. Continuously operating room-temperature devices are normally limited to moderate output power levels of a few milliwatts.

With the laser absorption spectrometers described herein, the tunable laser wavelength may be varied by changing the injection current while keeping the laser temperature constant. The temperature may be controlled by placing the laser in intimate contact with a thermoelectric cooler (Peltier cooler) whose temperature is measured with a thermistor and controlled by a feedback circuit.

In some implementations, an absorption spectrometer system may employ a harmonic spectroscopy technique in connection with its TDL light source. Harmonic spectroscopy as used in the disclosed subject matter involves the modulation of the TDL laser (DFB or VCSEL) wavelength at a high frequency (kHz-MHz) and the detection of the signal at a multiple of the modulation frequency. If the detection is performed at twice the modulation frequency, the term second harmonic or "2f" spectroscopy is used. Advantages to this technique include the minimization of 1/f noise, and the removal of the sloping baseline that is present on TDL spectra (due to the fact that the laser output power increases as the laser injection current increases, and changing the laser injection current is how the laser is tuned).

Figure 5:
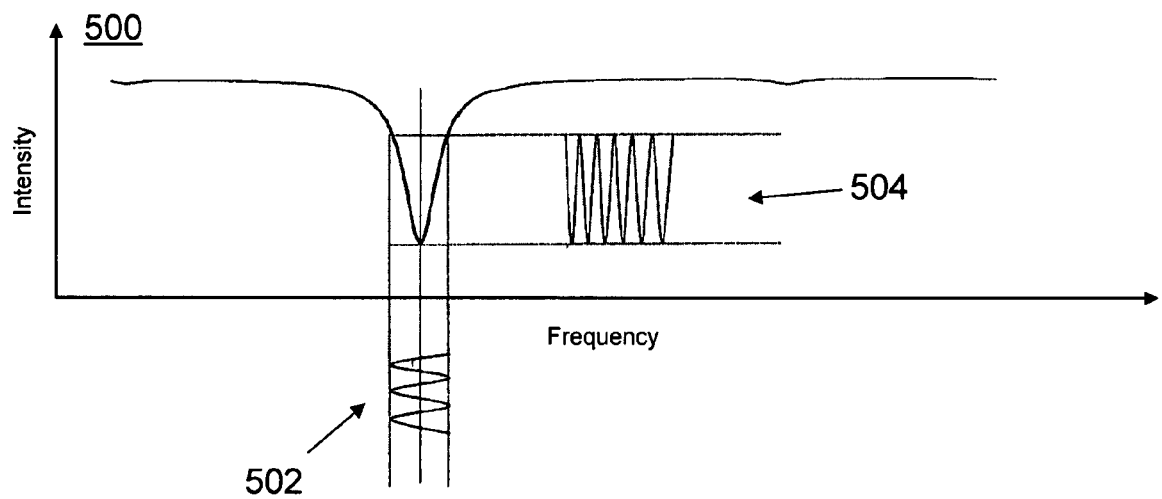
FIG. 5 is a chart that illustrates principles of wavelength modulation spectroscopy.
Figure 6:
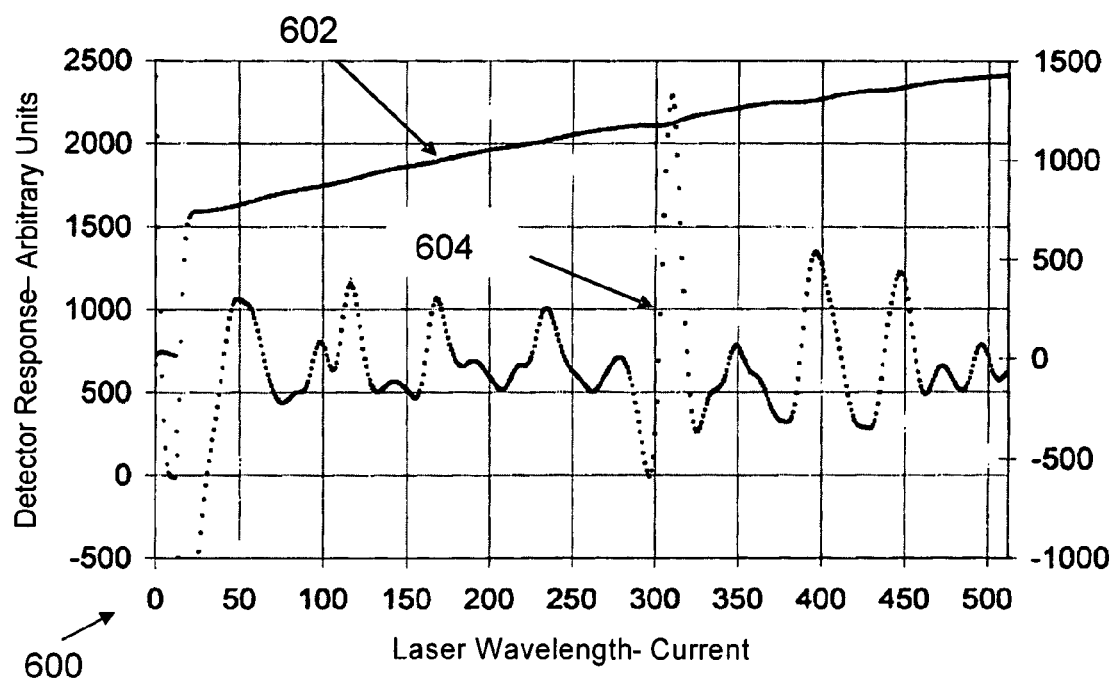
FIG. 6 is a chart showing an example of an absorption spectrum generated by a scan over a range of wavelengths encompassing a water absorption line.

FIG. 5 shows an example of a laser scan 500 for use in harmonic spectroscopy. A combination of a slow ramp and a fast sinusoidal modulation 502 is used to drive the diode laser. The photodetector receives this modulated intensity signal 504. The Nth harmonic component is resolved by demodulating the received signal. Detection using the signal at the second harmonic (2f) may be used. The 2f lineshape is symmetric and peaks at line center due to the nature of even function. Additionally, the second harmonic (2f) provides the strongest signal of the even-numbered harmonics. FIG. 6 presents a chart 600 of a typical laser intensity signal (DC) 602 and 2f lineshape 604 vs. frequency. By shifting detection to higher frequency, 2f spectroscopy can significantly reduce 1/f noise thus provides a substantial sensitivity enhancement compared to direct absorption methods.

In another implementation, a direct absorption spectroscopy may be used. In this implementation, the laser frequency is tuned over the selected absorption transition and the zero-absorption baseline may be obtained by fitting the regions outside the absorption line to a low-order polynomial. The integrated absorbance is directly proportional to the concentrations of absorbing species in the laser path length as well as the line strength of the transition. The absolute species concentration may be obtained without any calibration Photodetectors used in the disclosed absorption spectrometers depend on the specific wavelengths of the lasers and absorption lines to be measured. One photodetector is an indium gallium arsenide (InGaAs) photodiode sensitive to light in the 1200 to 2600 nm wavelength region. For longer wavelengths, an indium arsenide photodiode, sensitive for wavelengths up to approximately 3.6 µm, may be used. Alternatively, indium antimonide detectors are currently available for wavelengths as long as approximately 5.5 µm. Both of the indium devices operate in a photovoltaic mode and do not require a bias current for operation. These photodetectors, which lack low frequency noise, are advantageous for DC or low frequency applications. Such detectors are also advantageous for high speed pulse laser detection, making them particularly useful in trace gas absorption spectroscopy.

The gas analyzer may be controlled by a microprocessor that controls the laser current and synchronizes the laser current drive with the signal recording to facilitate detection of very low level signals. The detector signal processing and input/output to the user and data recording may be provided through direct interfaces with the microprocessor.

Figure 7:
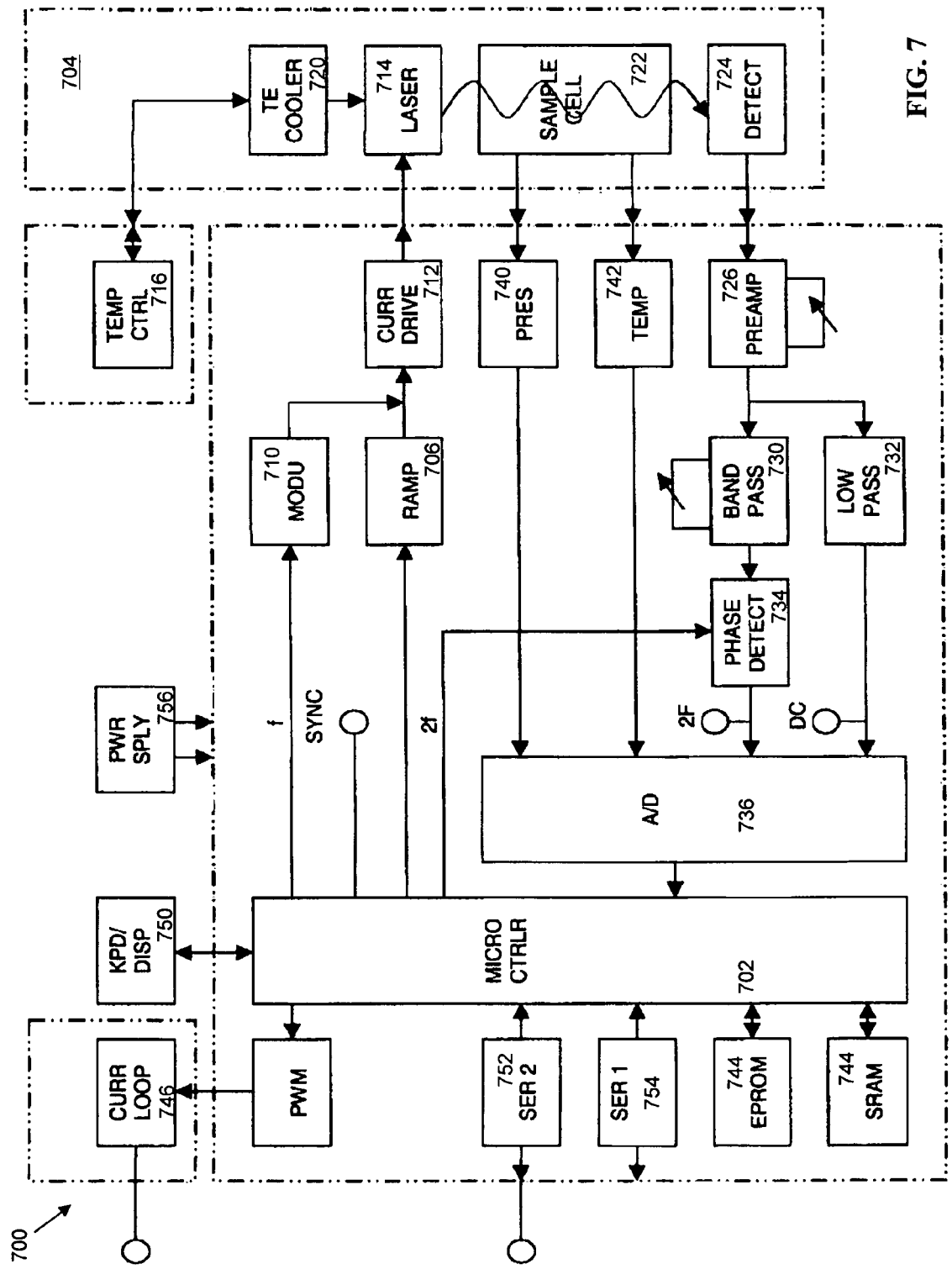
FIG. 7 is a block diagram of a measurement system.

FIG. 7 is a diagram of a sensor system 700 that includes a control and data processing loop system with a microprocessor 702 in communication with a spectrometer 704. On command, a signal is generated by the microprocessor 702 in the form of a rectangular pulse. This pulse is generated periodically. In one implementation, a 263 msec wide pulse is generated every 0.25 seconds. Other pulse widths and generation frequencies may be utilized. Each pulse is directed toward a ramp generator 706 that creates a DC signal, an example of which is shown diagrammatically in FIG. 8. In addition to the ramp signal, a modulating sine wave, at for example 7.5 KHz, may be imposed on the current ramp by a modulator 710 for later use in small signal detection. This combined signal is directed to the laser current driver 712 and on to the laser 714 itself.

In this implementation, the laser temperature is held constant by a temperature controller board 716 and the current varied for tuning the laser wavelength. The temperature control loop uses a thermistor (not shown) located close to the laser 714 as the temperature input and a thermoelectric cooler 720 mounted as close (thermally) to the laser 714 as possible. TECs and thermistors may be positioned either directly adjacent to the laser diode or externally to the laser diode enclosure. The temperature controller 716 may be used to set the exact laser wavelength such that variation of the driving current may provide the tuning range which may, for example, be in the range of approximately ±0.3 $cm^{-1}$.

At the beginning of each measurement cycle, the current is held to zero to read the signal produced by the photodetector without laser input and thereby provide the zero for that measurement cycle. This zero may vary a small amount due to slight changes in the detector dark current and the electronic noise so it is advantageous to measure it during each detector cycle. Following determination of the zero, the current is rapidly increased to the laser threshold current. This current is then increased over the remainder of the cycle until the peak current is reached. The beam created from this signal is directed through the sample cell 722 and onto the detector 724 which may be a photodiode array or other comparable detector. The output current from the detector is first amplified by a preamplifier 726. The output of the preamplifier is split and sent to a bandpass filter 730 and a lowpass filter 732. The bandpass filter 730 is a narrowband filter that singles out the 2f signal at 15 KHz and directs it to a lock-in amplifier 734 whose reference is set at 15 KHz from a signal provided by the microprocessor. The lock-in amplifier 734 further amplifies the signal and directs it to an A-D board 736 and back into the microprocessor 702. The lowpass filter 732 provides the detector output except the 2f signal. This signal provides the microprocessor 702 with the zero for the system and is also a diagnostic tool.

As was previously indicated, the signal is developed and recorded by the microprocessor 702 for each cycle of the analyzer. The processor determines the concentration of the gas sample of interest by computing the absorbance of the gas as a ratio between the zero and the measured value of absorbance at the peak of the absorbance line. The absorbance is a function of the gas pressure and temperature in the cell which are measured by appropriate means 740 and 742, respectively, whose outputs are supplied to the A/D board 736. The absorbance may be adjusted by a pressure/temperature calibration matrix stored in the microprocessor memory 744. This matrix is developed on an analyzer-by-analyzer basis. Alternatively, one or more corrective calculations may be performed based on measured temperature and pressure in the sample cell or cells.

Once the corrected absorbance value is determined, the concentration may be computed using equation 3. In one implementation, this concentration may be converted into units of, for example lbs/mmscf, averaged four times, and sent to the outputs once per second. Outputs that may be included in this system are a 4-20 mA current loop 746, a visual display 750 and RS-232 or comparable serial ports 752 and 754. Power for the system is provided by an appropriately chosen power supply 756.

Spectrometers described here accurately and repeatedly measure sub-part-per-million ($\leq$300 ppb) levels of water vapor ($H_2O$) in hydrocarbon gas mixtures, including but not limited to those containing ethylene, propylene and isobutane using a laser with appropriately selected wavelengths. A wavelength may be utilized if water molecules absorb light at a substantially greater level than do olefin gas molecules. More specifically, a relationship between the absorbance of water vapor in air and the dehumidified olefin mixture may be quantified using the following equation:

$$FOM = A_{H_2O,\lambda} / A_{GasMixture,\lambda} \quad (6)$$

where FOM is a "figure of merit," $A_{H_2O,\lambda}$ is the absorbance due to 100 ppm of water vapor at a given wavelength $\lambda$, and $A_{GasMixture,\lambda}$ is the absorbance of the dry hydrocarbon gas mixture at the wavelength $\lambda$. Both $A_{H_2O,\lambda}$ and $A_{GasMixture,\lambda}$ are measured at the same pressure and absorption path length. In one implementation, $A_{H_2O,\lambda}$ and $A_{GasMixture,\lambda}$ may be quantified at 1 atm pressure for a 1 m path length. A laser wavelength, $\lambda$, is usable if the FOM for that wavelength is greater than 0.001. In other words, the absorbance of water at the chosen wavelength must be at least one one-thousandth of the absorbance of the dry hydrocarbon mixture at the chosen wavelength. Table 1 lists a number of specific wavelengths for which this condition is satisfied.

TABLE 1

Examples of absorption transitions for $H_2O$ measurements in olefin gas mixtures.

| |
|---|
| 1359.5 nm |
| 1361.7 nm |
| 1368.6 nm |
| 1371.0 nm |
| 1392.2 nm |
| 1836.3 nm |
| 1840.0 nm |
| 1842.1 nm |
| 1847.1 nm |
| 1854.0 nm |
| 1856.7 nm |
| 1859.8 nm |
| 1877.1 nm |
| 1890.3 nm |
| 1899.7 nm |
| 1903.0 nm |
| 1905.4 nm |
| 2573.6 nm |
| 2583.9 nm |
| 2596.0 nm |
| 2605.6 nm |
| 2620.5 nm |
| 2626.7 nm |
| 2630.6 nm |
| 2665.1 nm |
| 2676.1 nm |
| 2711.2 nm |
| 2724.2 nm |
| 2735.0 nm |
| 2740.3 nm |

In one implementation, a wavelength may be validated as follows for use with the subject matter described herein. As a first step, an absorption cell path length is chosen. Some examples of path lengths for which absorption cells are readily available include but are not limited to 0.4 m, 0.8 m, 8 m, 28 m. If the FOM for the chosen wavelength is greater than 1, a path length is chosen to be greater than the minimum path length available (signal to noise ratio >1). If the FOM is between 0.01 and 1, the path length is chosen to be greater than 3 times the minimum path length available (signal to noise ratio >3). If the FOM is less than 0.01, the path length is chosen to be greater than the minimum path length (signal to noise ratio >1).

Next, the working pressure is determined. If the absorbance of the dry hydrocarbon gas mixture is greater than 1—in other words, no light is transmitted through the gas at the chosen path length and working pressure—the working pressure may need to be reduced below 1 atm. In this case, the absorption spectra for both the dehumified gas mixture and the mixture without dehumidification are recorded and analyzed at the new pressure. New tables are generated at the new working pressure, and the determination of an appropriate path length is repeated. If the background absorbance is less than 1, a working pressure of 1 atm may be used.

Finally, a decision is made whether to use a differential absorption scheme. If the FOM is less than 0.01, a differential absorption scheme is used, and the transition with the minimum path length and the maximum SNR is chosen from the available laser wavelengths. Alternatively, the transition with the minimum FOM and the maximum SNR may be chosen.

Figure 8:
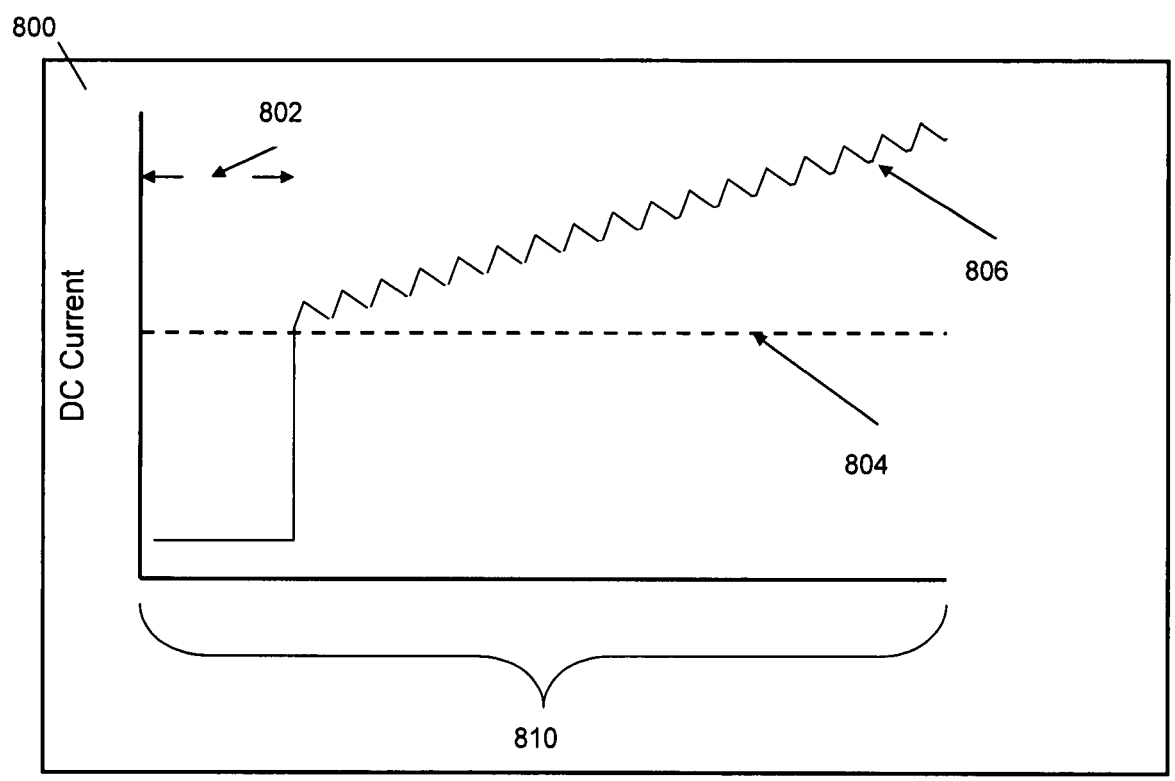
FIG. 8 is a chart showing an example of a laser current drive signal.

The chart of laser current vs. time 800 shown in FIG. 8 illustrates an example of the laser pulse profile that may be used in the disclosed analyzers. For each pulse cycle, A dynamic zero measurement is made during an initial period 802 when the laser current is well below the lasing threshold 804. Then, the laser current is ramped rapidly to at or above the lasing threshold 804, and a modulated laser tuning ramp with an alternating current voltage 806 is added to facilitate the 2f demodulation calculations as described above. At the end of the pulse cycle 810, the process is repeated. In one example, the pulse cycle last approximately 263 milliseconds. Other cycle periods are within the scope of this disclosure.

Figure 9:
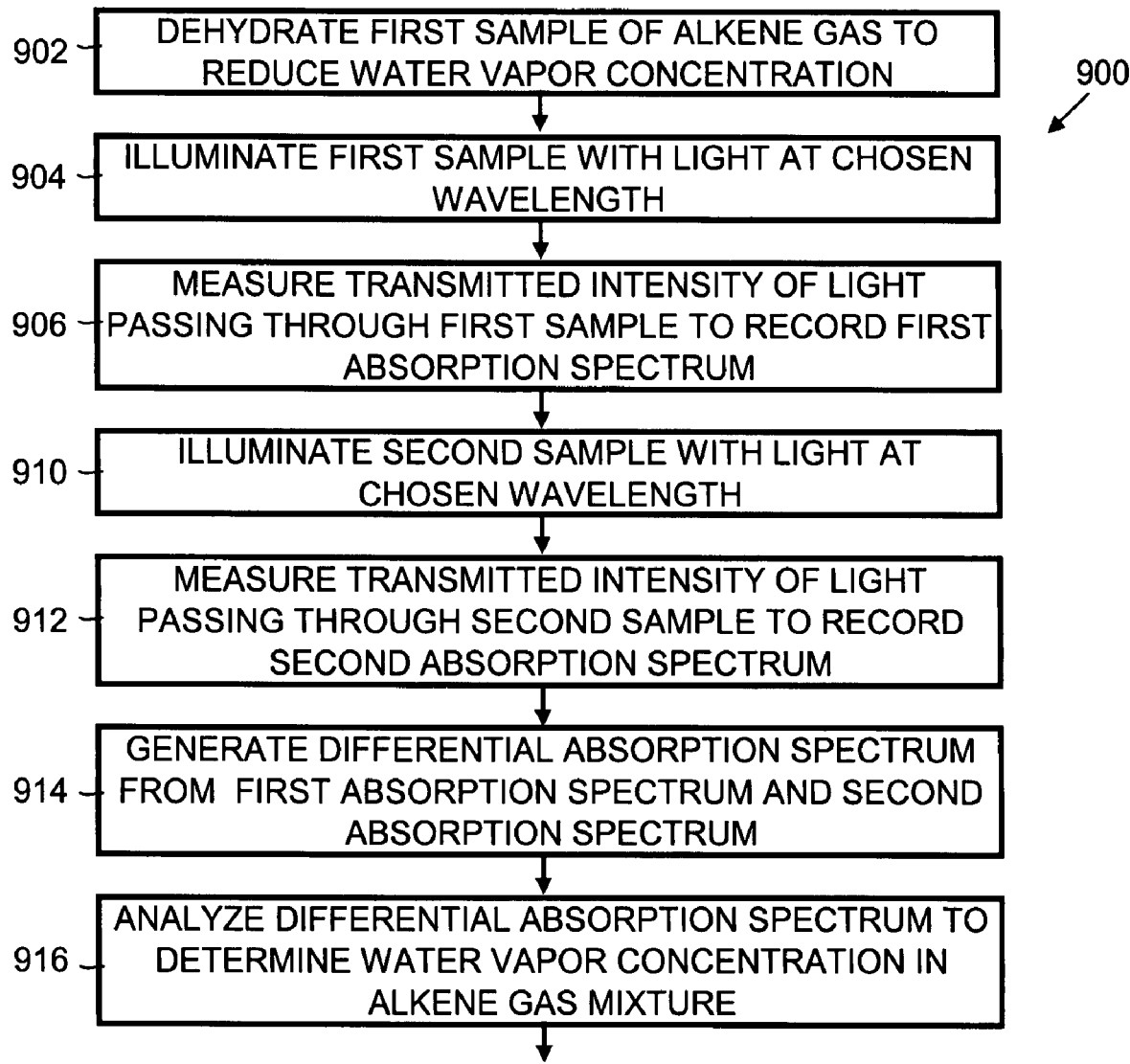
FIG. 9 is a process flow diagram illustrating a method of analyzing the water vapor concentration in a gas.

FIG. 9 shows a flow chart 900 of an example method of analyzing the water vapor concentration in a gas. In general, a first sample of the gas whose water vapor concentration is to be determined is dehydrated 902 to reduce the water vapor concentration. The dehydration process advantageously removes substantially all of the water vapor in the first sample to produce a reference or background sample of the gas that contains all of the gas components except water vapor. The first sample is illuminated with a beam of light from a light source at a chosen wavelength. This light source may advantageously be a laser, for example one of the lasers discussed above. The wavelength is chosen such that water molecules and the other components of the gas have resolvably different absorption features, for example as described above in regards to Table 1. The transmitted intensity of the light passing through the first sample is measured 906 and a first absorption spectrum is recorded. The measurement of transmitted intensity may be performed with a photodetector, for example one of those described above. The recording of the first absorption spectrum may be performed with a data analysis device, such as for example a microprocessor. A second sample of the gas is illuminated with light at the same chosen wavelength 910. The transmitted intensity of the light passing through the second sample is measured 912 and a second absorption spectrum is recorded. Again, a photodetector and data analysis device may be used. A differential absorption spectrum is generated form the first absorption spectrum and the second absorption spectrum 914, and this differential spectrum is analyzed to determine a concentration of water vapor in the gas. The measurements of transmitted intensity for the first and the second samples may be performed sequentially in a single sample cell or may be performed in parallel sample cells with identical optical path lengths.

Figure 10:
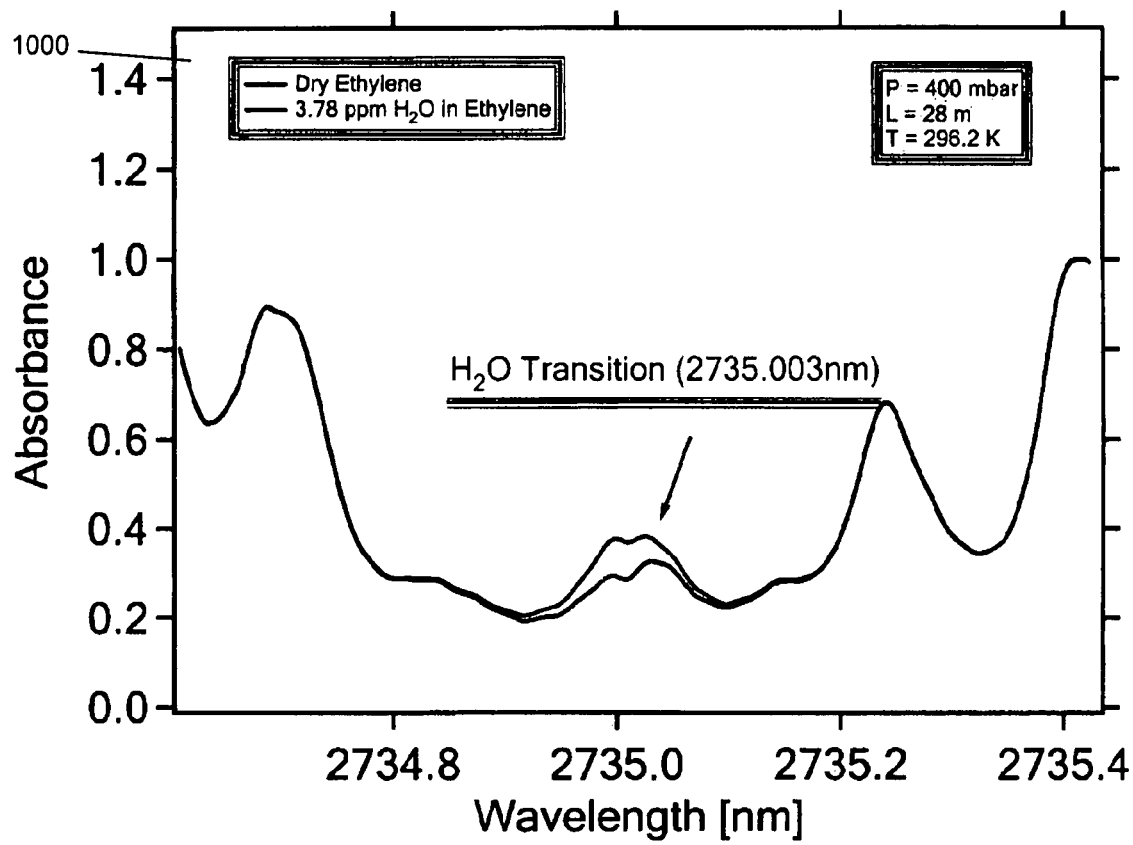
FIG. 10 is a chart showing absorption spectra of dry ethylene and ethylene with 3.78 ppm of water vapor.
Figure 11:
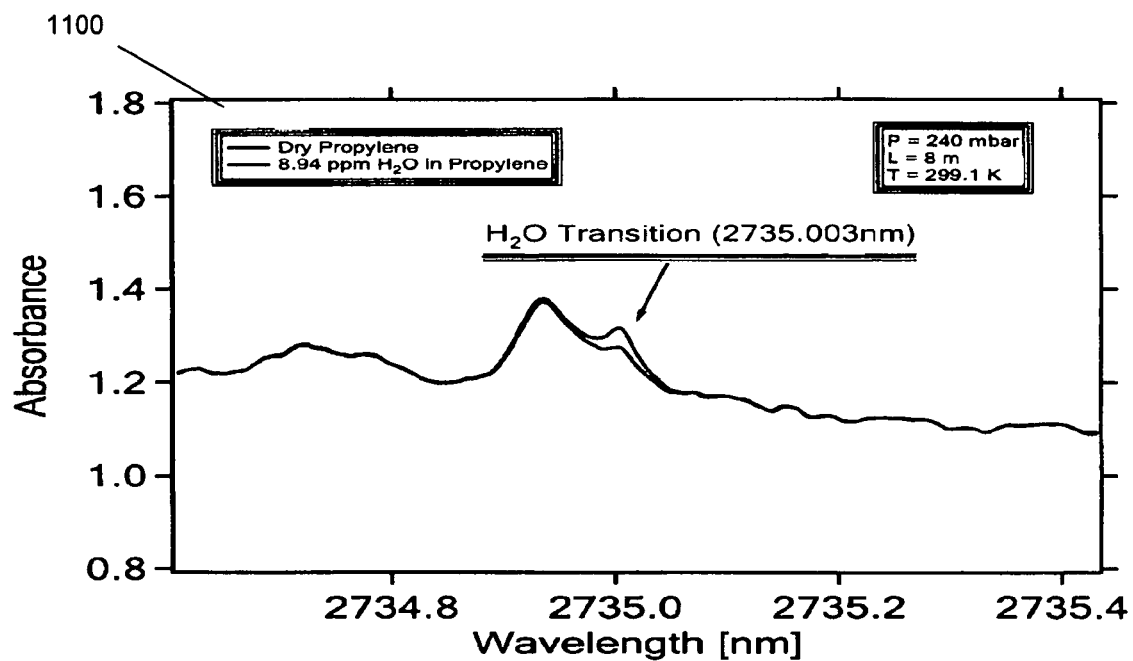
FIG. 11 is a chart showing absorption spectra of dry propylene and propylene with 8.94 ppm of water vapor.
Figure 12:
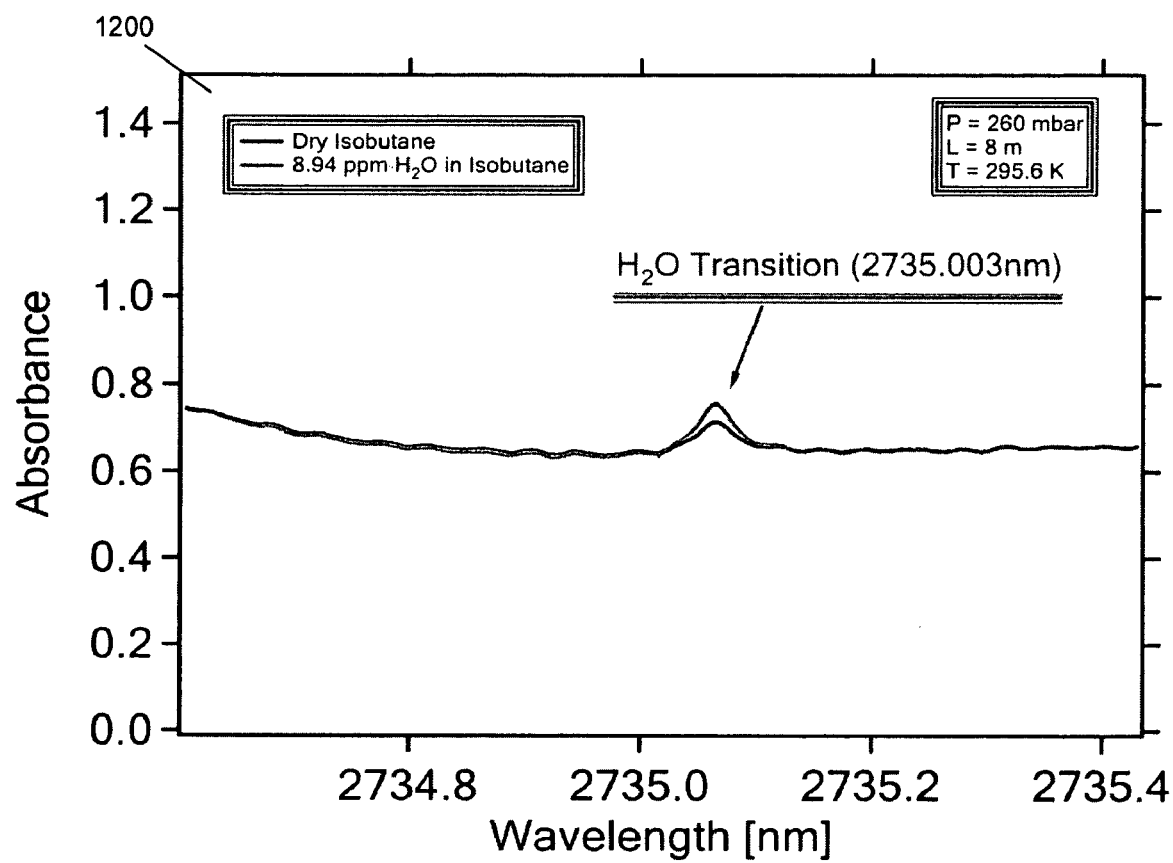
FIG. 12 is a chart showing absorption spectra of dry isobutane and isobutane with 8.94 ppm of water vapor.

FIG. 10, FIG. 11, and FIG. 12 show the overlapping spectra of ethylene, propylene, and isobutane, respectively, with water in the vicinity of approximately 2735 nm, which is one of the wavelengths identified in Table 1 above. The difference between the water absorption peak and those for these olefins in this region of the infrared spectrum is very small. As the absorption spectra graph 1000 in FIG. 10 shows, the difference is approximately $\leq 10$ mAU for ethylene. The absorption spectra graph 1100 in FIG. 11 shows that the difference is approximately $\leq 8$ mAU for propylene. The absorption spectra graph 1200 in FIG. 12 shows that the difference is approximately $\leq 6$ mAU for isobutane. However, by using the differential spectroscopic technique disclosed here and then peak seeking the "2f" signal, concentrations of water vapor in individual gas mixtures containing approximately 500 mBar partial pressure of each of these olefins may be performed. The measurement can also be effective at higher partial pressures of the background gas. For each measurement, the sample cell is maintained at an constant temperature within a range of approximately $\pm 1°$ C. Temperature control of the spectrometer is achieved by placing the spectrometer in a thermally controlled enclosure having an interior that is insulated with a temperature held above 30° C. in conditions where the environment can vary from $-15°$ C. to $+60°$ C.

To provide redundant measurements, the analyzers disclosed here may optionally further include a conventional water vapor analyzer 140 as shown in FIG. 1 and FIG. 2, such as for example a dew point measurement device, a piezoelectric adsorption device, a phosphorus pentoxide electrolysis device, or an aluminum or silicon oxide sensor.

EXAMPLES

Figure 13:
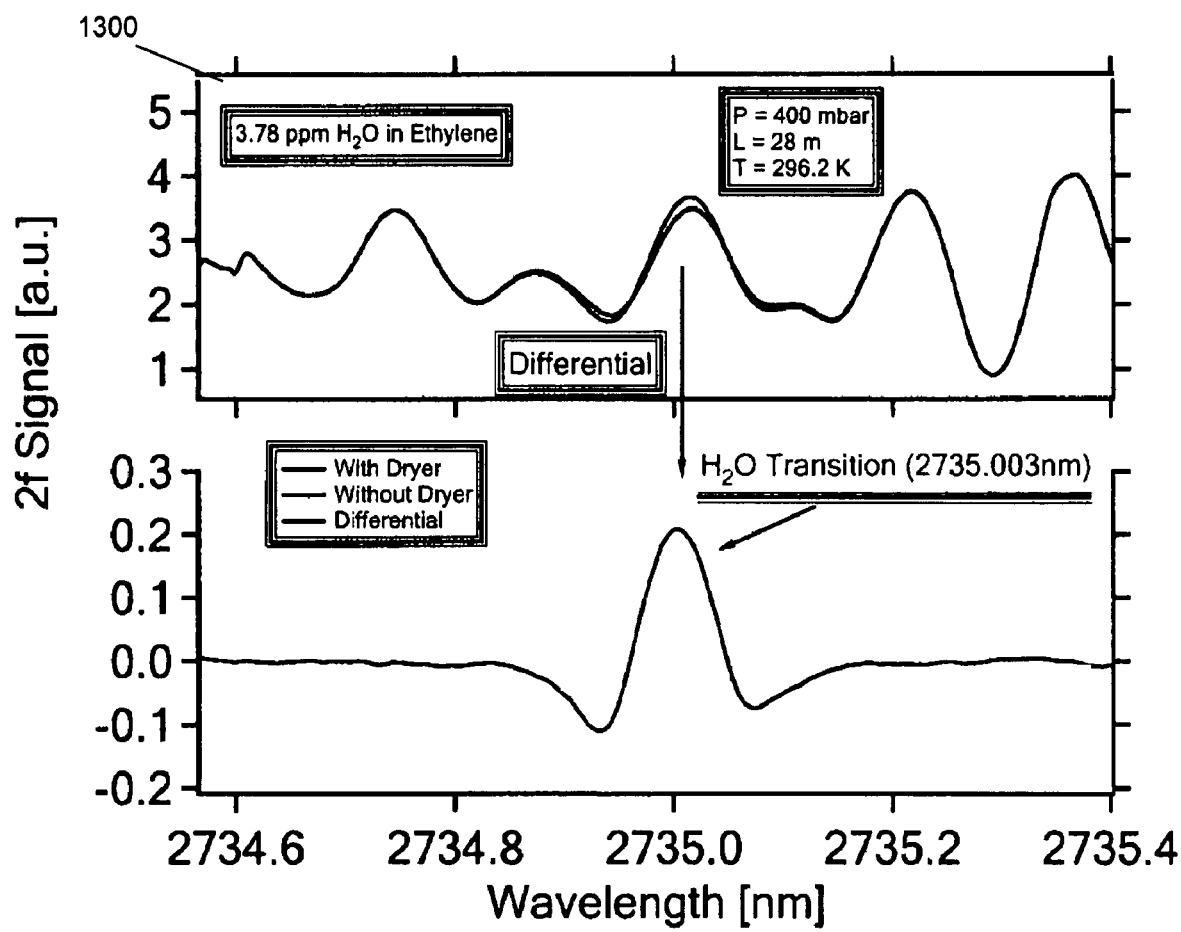
FIG. 13 is a chart showing absorption spectra measurements of differential spectra and a 2f signal for water vapor in ethylene.
Figure 14:
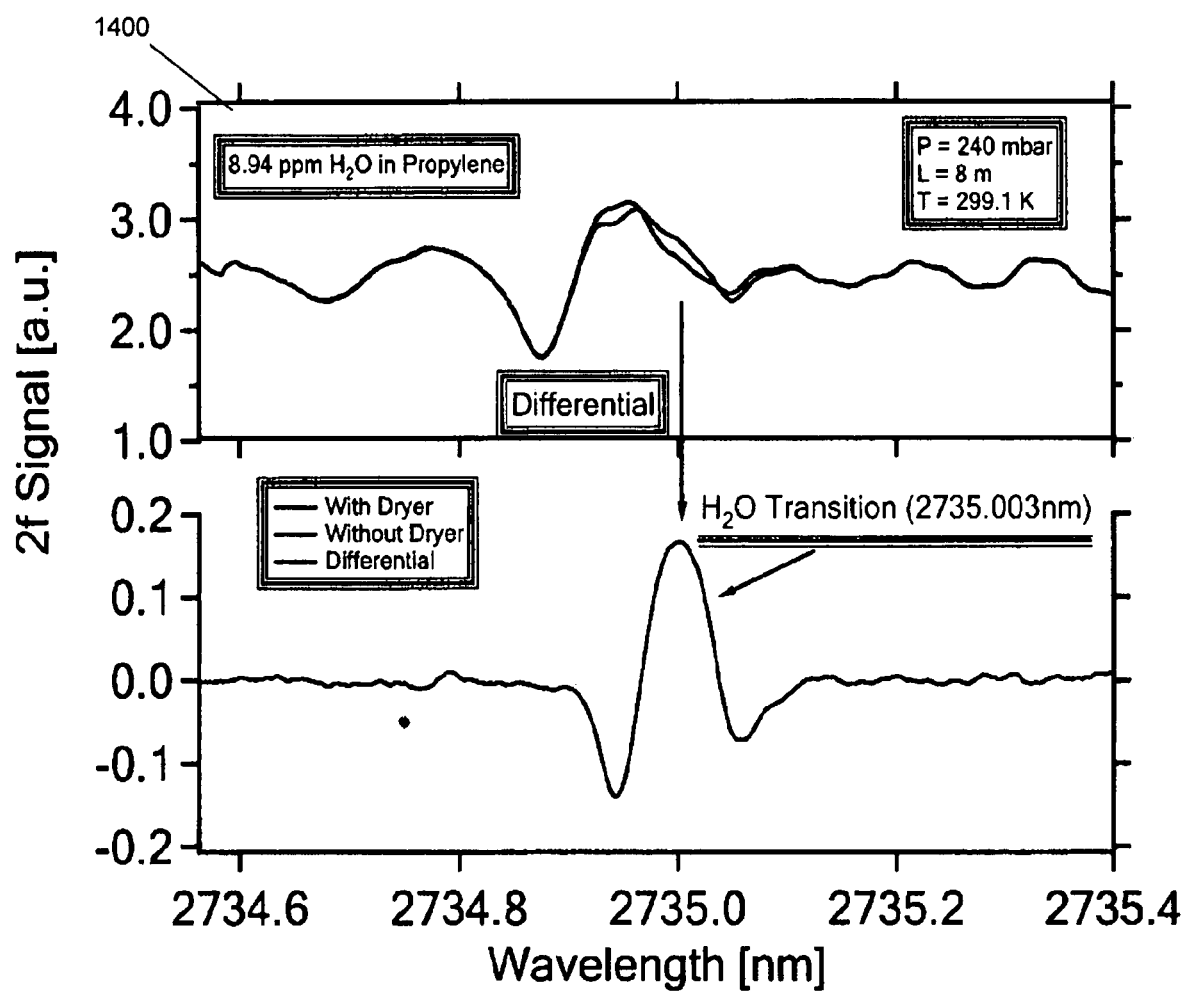
FIG. 14 is a chart showing absorption spectra measurements of differential spectra and a 2f signal for water vapor in propylene.
Figure 15:
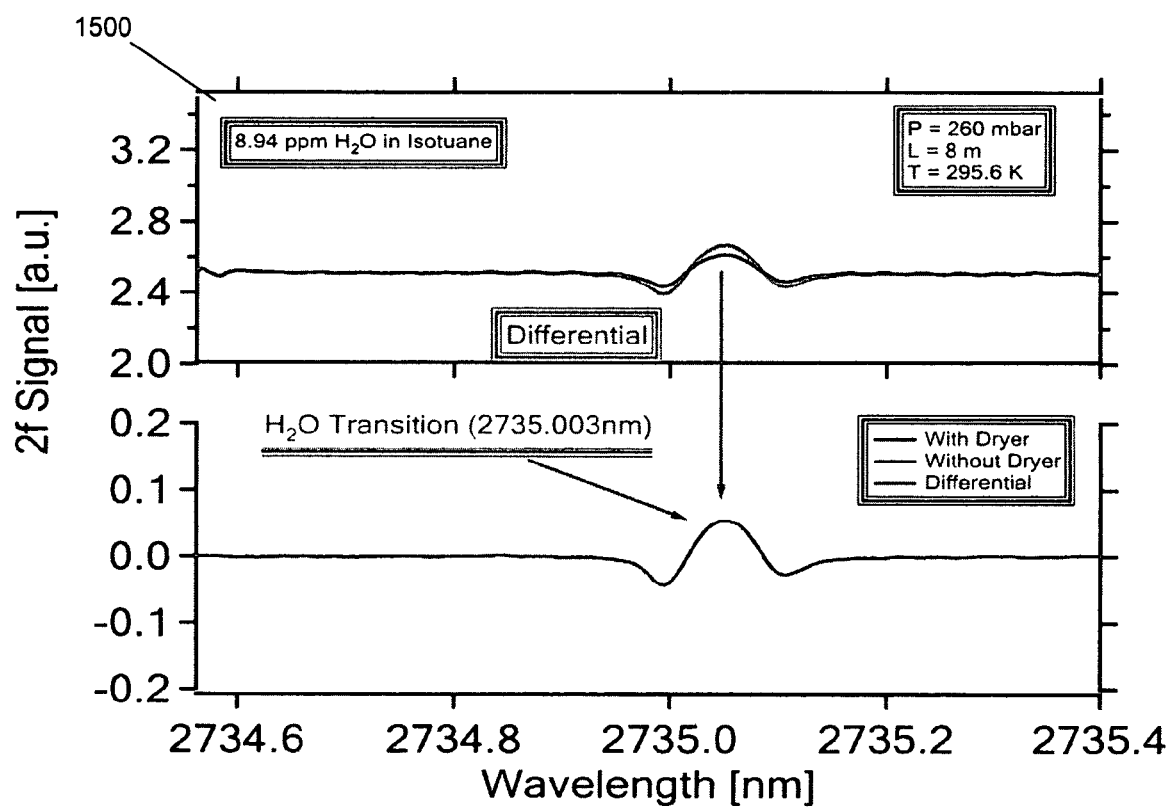
FIG. 15 is a chart showing absorption spectra measurements of differential spectra and a 2f signal for water vapor in isobutane.

Using techniques and spectrometers described herein, the curves shown in FIG. 13 for water vapor in 500 mBar partial pressure of ethylene, FIG. 14 for water vapor in 250 mBar partial pressure of propylene, and FIG. 15 for water vapor in 300 mBar partial pressure of isobutane were generated. For each example shown, a single sample cell configuration similar to that shown in FIG. 2 was used. A tunable laser operating a wavelength of approximately 2735 nm provided the incident light. The laser pulse cycle period was approximately 263 milliseconds, and the spectrometer's temperature was controlled by placing it in a thermally controlled cabinet held at a temperature above 30° C. with a precision of approximately $\pm 0.1°$ C.

The results of these examples demonstrate reproducible quantification of $\leq 500$ Ppb of $H_2O$ in gas mixtures containing olefins. For ethylene, an absorption cell whose total path length of approximately 28 meters long was used to produce the absorption spectra shown in the graph 1300 of FIG. 13. For propylene and isobutane, the path length was approximately 8 meters to produce the spectra shown in the graph 1400 of FIG. 14 and the graph 1500 of FIG. 15, respectively.

Although a few variations have been described in detail above, other modifications are possible. For example, the logic flow depicted in the accompanying figures and described herein do not require the particular order shown, or sequential order, to achieve desirable results. Other embodiments may be within the scope of the following claims.

What is claimed is:

1. A method comprising:
   dehydrating a first sample of an olefin gas mixture containing an unknown concentration of water vapor and a varying concentration of one or more olefins to reduce the water vapor concentration;
   recording a first absorption spectrum of the first sample at a chosen wavelength, the first absorption spectrum being recorded using a harmonic spectroscopy method;
   recording a second absorption spectrum of a second sample of the olefin gas mixture, the second absorption spectrum being obtained in parallel or sequentially with the first absorption spectrum, the second absorption spectrum being recorded using the harmonic spectroscopy method;
   generating a differential absorption spectrum from the first absorption spectrum and the second absorption spectrum;
   analyzing the differential spectrum to determine the concentration of water vapor in the olefin gas mixture.

2. A method as in claim 1, wherein the recording of the first absorption spectrum comprises: illuminating the first sample with light comprising the chosen wavelength, measuring a first transmitted intensity of light passing through the first sample, and passing the measured intensity to a data analysis device; and
   the recording of the second absorption spectrum comprises: illuminating the second sample with light comprising the chosen wavelength, measuring a second transmitted intensity of light passing through the second sample, and passing the measured intensity to the data analysis device.

3. A method as in claim 1, wherein the chosen wavelength is one at which water vapor has a resolvably different absorption feature than other components of the olefin gas mixture.

4. A method as in claim 1, wherein the chosen wavelength is absorbed at least approximately 0.001 times as strongly by air with a concentration of 100 ppm of water vapor as by dry air containing an olefin concentration approximately equivalent to that in the olefin gas mixture.

5. A method as in claim 1, wherein the chosen wavelength is selected from 1359.5 nm, 1856.7 nm, 2605.6 nm, 1361.7 nm, 1859.8 nm, 2620.5 nm, 1368.6 nm, 1877.1 nm, 2626.7 nm, 1371.0 nm, 1890.3 nm, 2630.6 nm, 1392.2 nm, 1899.7 nm, 2665.1 nm, 1836.3 nm, 1903.0 nm, 2676.1 nm, 1840.0 nm, 1905.4 nm, 2711.2 nm, 1842.1 nm, 2573.6 nm, 2724.2 nm, 1847.1 nm, 2583.9 nm, 2735.0 nm, 1854.0 nm, 2596.0 nm, and 2740.3 nm.

6. A method as in claim 1, further comprising providing a beam of laser light at the chosen wavelength from a tunable diode laser.

7. A method as in claim 1, wherein the first absorption spectrum and the second absorption spectrum are recorded sequentially in a single sample cell.

8. A method as in claim 1, further comprising maintaining the first and the second sample at a constant temperature.

9. A method as in claim 1, further comprising measuring the concentration of water vapor in the olefin gas mixture using one of a dew point sensor, a piezoelectric adsorption sensor, a phosphorus pentoxide electrolysis sensor, and an aluminum or silicon oxide sensor.

10. A method as in claim 1, wherein: the recording of the first absorption spectrum comprises collecting first intensity data as a function of wavelength for infrared light from a tunable diode laser passing through the first sample, the infrared light from the tunable diode laser being tuned through a chosen wavelength at which water vapor has an absorption feature that is resolvable from other absorption features of other components of the olefin gas mixture at the chosen wavelength, the infrared light having a spectral width that is narrower than the absorption feature; and the recording of the second absorption spectrum comprises collecting second intensity data as a function of wavelength for the infrared light from the tunable diode laser passing through the second sample.

11. A method as in claim 10, wherein a frequency of the infrared light from the tunable diode laser is modulated at a modulation frequency; and the recording of the first absorption spectrum and the second absorption spectrum comprises resolving harmonic signals for the first intensity data and the second intensity data at a multiple of the modulation frequency.

12. A method as in claim 10, further comprising obtaining a zero-absorption baseline by fitting the first intensity data and/or the second intensity data to a low-order polynomial for one or more frequency ranges outside of the chosen wavelength through which the infrared light from the tunable diode laser is tuned; and using the zero-absorption baseline to determine the concentration of water vapor in the olefin gas mixture without the use of calibration data.

13. A method as in claim 1, wherein the recording of the first absorption spectrum comprises: illuminating the first sample with light comprising the chosen wavelength, measuring a first transmitted intensity of light passing through the first sample, and passing the measured intensity to a data analysis device; and the recording of the second absorption spectrum comprises: illuminating the second sample with light comprising the chosen wavelength, measuring a second transmitted intensity of light passing through the second sample, and passing the measured intensity to the data analysis device.

14. A method comprising:
dehydrating a first sample of an olefin gas mixture containing an unknown concentration of water vapor and a varying concentration of one or more olefins to reduce the water vapor concentration;
recording a first absorption spectrum of the first sample at a chosen wavelength;
recording a second absorption spectrum of a second sample of the olefin gas mixture, the second absorption spectrum being obtained in parallel or sequentially with the first absorption spectrum, the first absorption spectrum and the second absorption spectrum being recorded in parallel in first and second sample cells with substantially identical optical path lengths;
generating a differential absorption spectrum from the first absorption spectrum and the second absorption spectrum; and
analyzing the differential spectrum to determine the concentration of water vapor in the olefin gas mixture.

15. A method as in claim 14, wherein the first absorption spectrum and the second absorption spectrum are recorded using a harmonic spectroscopy method.

16. A method as in claim 14, wherein the chosen wavelength is selected from 1359.5 nm, 1856.7 nm, 2605.6 nm, 1361.7 nm, 1859.8 nm, 2620.5 nm, 1368.6 nm, 1877.1 nm, 2626.7 nm, 1371.0 nm, 1890.3 nm, 2630.6 nm, 1392.2 nm, 1899.7 nm, 2665.1 nm, 1836.3 nm, 1903.0 nm, 2676.1 nm, 1840.0 nm, 1905.4 nm, 2711.2 nm, 1842.1 nm, 2573.6 nm, 2724.2 nm, 1847.1 nm, 2583.9 nm, 2735.0 nm, 1854.0 nm, 2596.0 nm, and 2740.3 nm.

17. An apparatus comprising:
a modulated laser light source that emits light comprising a chosen wavelength;
a sample cell;
a dehydrator that reduces water vapor in a first sample of an olefin gas mixture, the olefin gas mixture containing a varying concentration of one or more olefins and, prior to entering the dehydrator, an unknown concentration of water vapor;
one or more valves for alternately and sequentially providing the first sample and a second sample of the olefin gas mixture to the sample cell, the second sample containing the unknown water vapor concentration of the olefin gas mixture;
a photodetector positioned to quantify light passing through the sample cell; and
a microprocessor that records a first absorption spectrum from the photodetector using a harmonic spectroscopy method when the sample cell contains the first sample, records a second absorption spectrum from the photodetector using the harmonic spectroscopy method when the sample cell contains the second sample, calculates a differential absorption spectrum from the first and second absorption spectra, and calculates the concentration of water vapor in the olefin gas mixture based on the differential absorption spectrum.

18. An apparatus as in claim 17, wherein the laser light source is a tunable diode laser.

19. An apparatus as in claim 17, wherein the laser light source is selected from a vertical cavity surface emitting laser, a horizontal cavity surface emitting laser, a quantum cascade laser, a distributed feedback laser, and a color center laser.

20. An apparatus as in claim 17, wherein the chosen wavelength is absorbed at least approximately 0.001 times as strongly by air with a concentration of 100 ppm of water vapor as by dry air containing an olefin concentration approximately equivalent to that in the olefin gas mixture.

21. An apparatus as in claim 17, wherein the chosen wavelength is selected from 1359.5 nm, 1856.7 nm, 2605.6 nm, 1361.7 nm, 1859.8 nm, 2620.5 nm, 1368.6 nm, 1877.1 nm, 2626.7 nm, 1371.0 nm, 1890.3 nm, 2630.6 nm, 1392.2 nm, 1899.7 nm, 2665.1 nm, 1836.3 nm, 1903.0 nm, 2676.1 nm, 1840.0 nm, 1905.4 nm, 2711.2 nm, 1842.1 nm, 2573.6 nm, 2724.2 nm, 1847.1 nm, 2583.9 nm, 2735.0 nm, 1854.0 nm, 2596.0 nm, and 2740.3 nm.

22. An apparatus as in claim 17, further comprising a thermally controlled chamber that encloses one or more of the laser light source, the photodetector, and the sample cell.

23. An apparatus as in claim 17, further comprising:
an additional water vapor concentration analyzer selected from a dew point measurement device, a piezoelectric adsorption device, a phosphorus pentoxide electrolysis device, and an aluminum or silicon oxide sensor.

24. An apparatus comprising:
a laser light source that emits light comprising a chosen wavelength;
a dehydrator to reduce water vapor in a first sample of an olefin gas mixture, the olefin gas mixture containing an unknown concentration of water vapor and a varying concentration of one or more olefins;
a first sample cell for containing the first sample;
a second sample cell for containing a second sample of the olefin gas mixture, wherein the second sample cell has a substantially identical path length to the first sample cell;
a gas flow divider that directs the first sample to the first sample cell and the second sample to the second sample cell for parallel analysis;
optical components for splitting the beam between the first sample cell and the second sample cell;
a first photodetector positioned to quantify light passing through the first sample cell;
a second photodetector positioned to quantify light passing through the second sample cell; and
a microprocessor that records a first absorption spectrum from the first photodetector, records a second absorption spectrum from the second photodetector, calculates a differential absorption spectrum from the first and second absorption spectra, and calculates the concentration of water vapor in the olefin gas mixture based on the differential absorption spectrum.

25. An apparatus as in claim 24, wherein the laser light source is a tunable diode laser.

26. An apparatus as in claim 25, wherein the laser source is modulated and the first and the second absorption spectra are harmonic absorption spectra.

27. An apparatus as in claim 25, wherein the laser source is modulated and the first and the second absorption spectra are direct absorption spectra.

28. An apparatus as in claim 24, wherein the laser light source is selected from a vertical cavity surface emitting laser, a horizontal cavity surface emitting laser, a quantum cascade laser, a distributed feedback laser, and a color center laser.

29. An apparatus as in claim 24, wherein the chosen wavelength is absorbed at least approximately 0.001 times as strongly by air with a concentration of 100 ppm of water vapor as by dry air containing an olefin concentration approximately equivalent to that in the olefin gas mixture.

30. An apparatus as in claim 24, wherein the chosen wavelength is selected from 1359.5 nm, 1856.7 nm, 2605.6 nm, 1361.7 nm, 1859.8 nm, 2620.5 nm, 1368.6 nm, 1877.1 nm, 2626.7 nm, 1371.0 nm, 1890.3 nm, 2630.6 nm, 1392.2 nm, 1899.7 nm, 2665.1 nm, 1836.3 nm, 1903.0 nm, 2676.1 nm, 1840.0 nm, 1905.4 nm, 2711.2 nm, 1842.1 nm, 2573.6 nm, 2724.2 nm, 1847.1 nm, 2583.9 nm, 2735.0 nm, 1854.0 nm, 2596.0 nm, and 2740.3 nm.

31. An apparatus as in claim 24, further comprising:
a thermally controlled chamber that encloses one or more of the laser source, the first photodetector, the second photodetector, the first sample cell and the second sample cell.

32. An apparatus as in claim 24, further comprising:
an additional water vapor concentration analyzer selected from a dew point measurement device, a piezoelectric adsorption device, a phosphorus pentoxide electrolysis device, and an aluminum or silicon oxide sensor.

33. An apparatus comprising:
means for generating a beam of light at a wavelength where water molecules and other components of an olefin gas mixture have different absorbances, the olefin gas mixture containing an unknown water vapor concentration and varying concentrations of two or more olefins;
means for reducing water vapor in a first sample of the olefin gas mixture;
means for illuminating the first sample of the gas with the beam and recording a first absorbance spectrum;
means for illuminating a second sample of the olefin gas mixture with the beam and recording a second absorbance spectrum, the second sample being illuminated in parallel or sequentially with the first sample;
processing means for generating and analyzing a differential absorbance spectrum from the first absorbance spectrum and the second absorbance spectrum to determine the concentration of water vapor in the olefin gas mixture.

\* \* \* \* \*